(12) United States Patent
Monirabbasi et al.

(10) Patent No.: US 11,031,114 B2
(45) Date of Patent: Jun. 8, 2021

(54) METHODS FOR OPERATING MODE TRANSITIONS AND RELATED INFUSION DEVICES AND SYSTEMS

(71) Applicant: MEDTRONIC MINIMED, INC., Northridge, CA (US)

(72) Inventors: Salman Monirabbasi, Playa Vista, CA (US); Louis J. Lintereur, Stevenson Ranch, CA (US); Jin Yan, Chatsworth, CA (US); Linda I. Torres, Moorpark, CA (US)

(73) Assignee: MEDTRONIC MINIMED, INC, Northridge, CA (US)

( * ) Notice: Subject to any disclaimer, the term of this patent is extended or adjusted under 35 U.S.C. 154(b) by 421 days.

(21) Appl. No.: 15/908,757

(22) Filed: Feb. 28, 2018

(65) Prior Publication Data
US 2018/0185578 A1 Jul. 5, 2018

Related U.S. Application Data

(63) Continuation of application No. 14/561,133, filed on Dec. 4, 2014, now Pat. No. 9,943,645.

(51) Int. Cl.
*G16H 20/17* (2018.01)
*A61M 5/172* (2006.01)
(Continued)

(52) U.S. Cl.
CPC .......... *G16H 20/17* (2018.01); *A61M 5/1424* (2013.01); *A61M 5/14244* (2013.01);
(Continued)

(58) Field of Classification Search
CPC ........ A61M 5/1723; A61M 2005/1726; A61M 5/14244; A61M 5/172;
(Continued)

(56) References Cited

U.S. PATENT DOCUMENTS 4,206,755 A * 6/1980 Klein .................. A61M 5/1723
600/368
4,562,751 A 1/1986 Nason et al.
(Continued)

FOREIGN PATENT DOCUMENTS

CN 1973768 A 6/2007
CN 201996544 U 10/2011
(Continued)

*Primary Examiner* — Emily L Schmidt
*Assistant Examiner* — Leah J Swanson

(57) ABSTRACT

Infusion systems, infusion devices, and related operating methods are provided. An exemplary method involves operating an infusion device to deliver fluid to a user in accordance with a first operating mode of a plurality of operating modes, obtaining operational information pertaining to the first operating mode, and obtaining clinical information pertaining to the user. A destination operating mode of the plurality of operating modes is determined based at least in part on the operational information and the clinical information, and the infusion device is operated to deliver the fluid in accordance with the destination operating mode in a manner that is influenced by at least a portion of the operational information pertaining to the first operating mode.

20 Claims, 10 Drawing Sheets

(51) Int. Cl.
*A61M 5/142* (2006.01)
*G16H 40/63* (2018.01)
*G16H 20/13* (2018.01)

(52) U.S. Cl.
CPC .......... *A61M 5/172* (2013.01); *A61M 5/1723* (2013.01); *G16H 20/13* (2018.01); *G16H 40/63* (2018.01); *A61M 2005/14208* (2013.01); *A61M 2205/50* (2013.01); *A61M 2205/52* (2013.01)

(58) Field of Classification Search
CPC .... A61M 2005/14208; A61M 2205/50; A61M 2205/52; G16H 20/13; G16H 20/17; G16H 40/63
See application file for complete search history.

(56) References Cited

U.S. PATENT DOCUMENTS

| | | | |
|---|---|---|---|
| 4,685,903 A | 8/1987 | Cable et al. |
| 4,755,173 A | 7/1988 | Konopka et al. |
| 4,756,706 A | 7/1988 | Kerns et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,976,492 B2 | 7/2011 | Brauker et al. |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,282,625 B2 | 10/2012 | Ullestad et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,562,587 B2 | 10/2013 | Kovatchev et al. |
| 8,674,288 B2 | 3/2014 | Hanson et al. |
| 9,211,377 B2 | 12/2015 | DiPerna et al. |
| 2004/0122353 A1 | 6/2004 | Shahmirian et al. |
| 2005/0038332 A1* | 2/2005 | Saidara ............... A61B 5/0002 600/347 |
| 2007/0123819 A1 | 5/2007 | Mernoe et al. |
| 2008/0269714 A1 | 10/2008 | Mastrototaro et al. |
| 2008/0300572 A1 | 12/2008 | Rankers et al. |
| 2009/0156924 A1* | 6/2009 | Shariati ............. A61B 5/14546 600/365 |
| 2010/0160861 A1 | 6/2010 | Causey, III et al. |
| 2011/0098674 A1 | 4/2011 | Vicente et al. |
| 2011/0257627 A1 | 10/2011 | Hovorka |
| 2012/0010600 A1 | 1/2012 | Wilinska et al. |
| 2012/0323100 A1 | 12/2012 | Kamath et al. |
| 2012/0323212 A1 | 12/2012 | Murphy et al. |
| 2013/0317753 A1 | 11/2013 | Kamen et al. |
| 2014/0107607 A1 | 4/2014 | Estes |
| 2014/0221966 A1 | 8/2014 | Buckingham et al. |

FOREIGN PATENT DOCUMENTS

| | | |
|---|---|---|
| CN | 102946923 A | 2/2013 |
| EP | 1703143 A1 | 9/2006 |
| WO | 2014036177 A1 | 3/2014 |

* cited by examiner

METHODS FOR OPERATING MODE TRANSITIONS AND RELATED INFUSION DEVICES AND SYSTEMS

CROSS-REFERENCE TO RELATED APPLICATIONS

This application is a continuation of U.S. patent application Ser. No. 14/561,133, filed Dec. 4, 2014.

TECHNICAL FIELD

Embodiments of the subject matter described herein relate generally to medical devices, and more particularly, embodiments of the subject matter relate to managing transitions into fluid infusion device operating modes.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner. For example, an insulin infusion pump may operate in a closed-loop operating mode overnight while a user is sleeping to regulate the user's glucose level to a target glucose level. In practice, multiple different operating modes for providing continuous insulin infusion may be supported by an infusion pump. However, care must be taken when transitioning between operating modes to avoid potentially compromising a user's condition and ensure compliance with applicable regulatory requirements.

Additionally, in some situations, one or more preconditions must be satisfied before entering to a particular operating mode is allowed. When preconditions are not satisfied, entry into the operating mode may be denied, which may frustrate a user who would like to operate the infusion pump in that particular operating mode at that particular moment in time. Additionally, after entering a particular operating mode, various conditions may be encountered while operating the infusion pump in that operating mode that result in generation of alerts, which could be disruptive or distracting to the user. Thus, it is desirable to provide multiple different operating modes that facilitate greater and more customizable control over the user's physiological condition without degrading the user experience.

BRIEF SUMMARY

Infusion devices, systems and related methods of operation in accordance with various operating modes are provided. One exemplary method of operating an infusion device to deliver fluid to a user in accordance with an operating mode involves obtaining operational information pertaining to one or more prior instances of the operating mode, obtaining status information pertaining to the infusion device, and determining a diagnosis time based at least in part on the operational information. The diagnosis time is prior to a subsequent instance of the operating mode. At the diagnosis time, the method automatically determines the viability of the subsequent instance of the operating mode based at least in part on the status information and automatically generates a notification indicative of a recommended action for the user based at least in part on the viability.

In one embodiment, an infusion device is provided. The infusion device includes a user interface, a data storage element to maintain status information pertaining to the infusion device, a motor operable to deliver fluid influencing a physiological condition to a body of a user, and a control system. The control system is coupled to the motor, the data storage element, and the user interface. The control system operates the motor in a first instance of an operating mode to deliver the fluid in accordance with the operating mode, stores operational information pertaining to the first instance of the operating mode in the data storage element, and determines a diagnosis time based at least in part on the operational information pertaining to the first instance of the operating mode. At the diagnosis time, the control system automatically determines the viability of a subsequent instance of the operating mode based at least in part on the status information and automatically provides a notification indicative of a recommended action via the user interface based at least in part on the viability.

An embodiment of an infusion system is also provided. The infusion system includes a user interface, a sensing arrangement to obtain measurements of a physiological condition in a body of a user, and an infusion device coupled to the user interface and the sensing arrangement. The infusion device delivers fluid influencing the physiological condition to the body of the user based at least in part on the measurements in accordance with an operating mode. The infusion device maintains status information pertaining to operation of the infusion device and operational information pertaining to one or more previous instances of the operating mode, and determines a diagnosis time in advance of an expected start time for a subsequent instance of the operating mode based at least in part on the operational information. At the diagnosis time, the infusion device automatically determines the viability of the subsequent instance of the operating mode based at least in part on the status information and automatically provides a notification indicative of a recommended action via the user interface based at least in part on the viability.

In another embodiment, a method involves operating an infusion device to deliver fluid to a user in accordance with a first operating mode of a plurality of operating modes, obtaining operational information pertaining to the first operating mode, and obtaining clinical information pertaining to the user. The method continues by determining a destination operating mode of the plurality of operating modes based at least in part on the operational information and the clinical information, and operating the infusion device to deliver the fluid in accordance with the destination operating mode in a manner that is influenced by at least a portion of the operational information pertaining to the first operating mode.

Another embodiment of an infusion device includes a data storage element to maintain operational information pertaining to a first operating mode of a plurality of operating modes and clinical information pertaining to a user, a motor operable to deliver fluid influencing a physiological condition to a body of the user, and a control system coupled to the motor and the data storage element. The control system operates the motor to deliver the fluid in accordance with the first operating mode, determines a destination operating mode of the plurality of operating modes based at least in part on the operational information and the clinical information, and operates the infusion device to deliver the fluid in accordance with the destination operating mode in a manner that is influenced by at least a portion of the operational information pertaining to the first operating mode.

In yet another embodiment, a method of operating an infusion device operable to deliver insulin to a user involves operating the infusion device to deliver the insulin in accordance with a first operating mode of a plurality of operating modes, obtaining operational information pertaining to the first operating mode, and obtaining one or more glucose values for the user. In response to an indication to terminate the first operating mode, the method continues by determining a set of one or more possible operating modes from the plurality of operating modes based at least in part on the one or more glucose values and the operational information. The method selects a destination operating mode from the set of one or more possible operating modes and operates the infusion device to deliver the insulin in accordance with the destination operating mode in a manner that is influenced by at least a portion of the operational information pertaining to the first operating mode.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
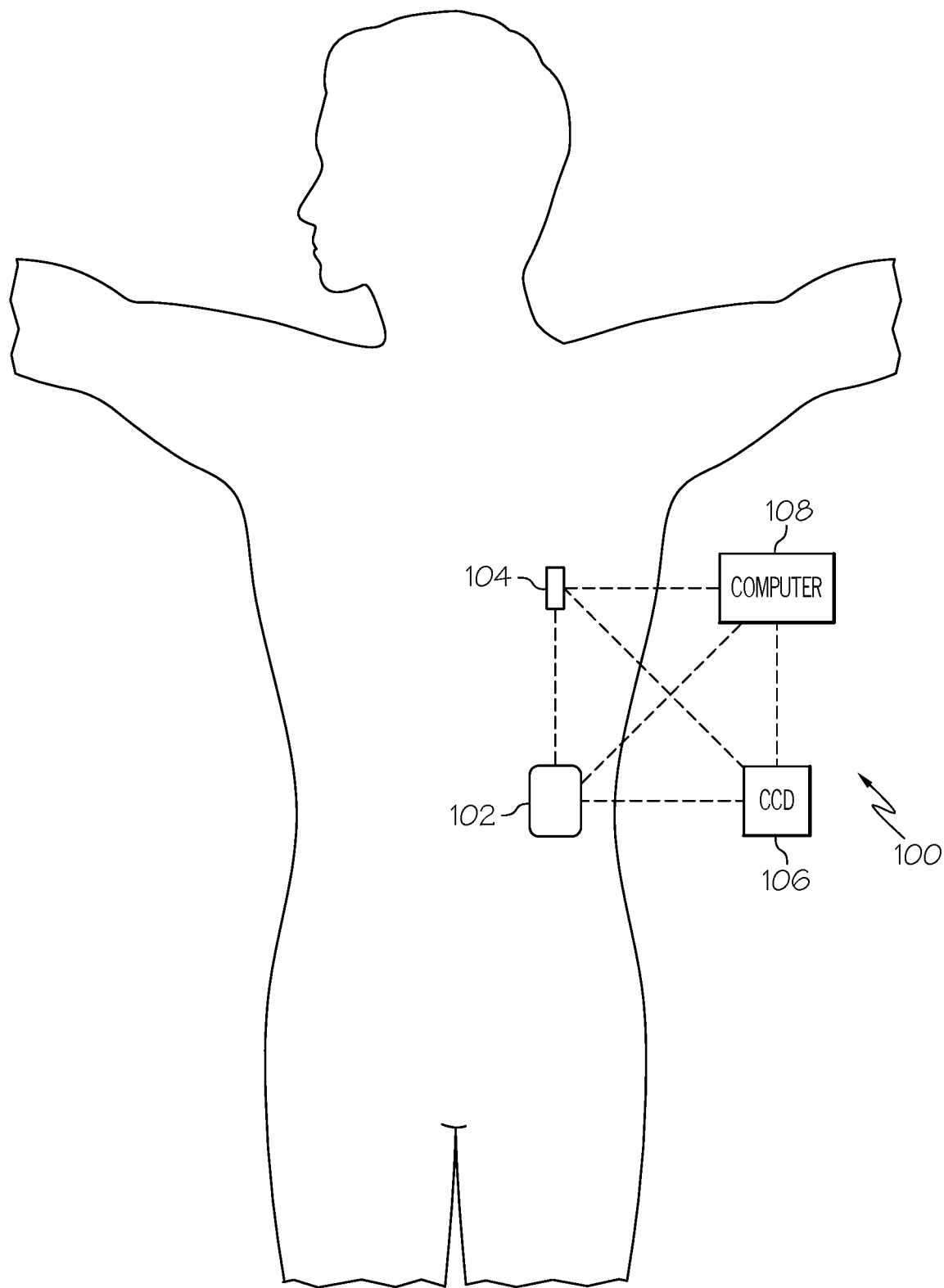
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode. For example, in a closed-loop operating mode, the dosage commands are generated based on a difference between a current (or most recent) measurement of a physiological condition in the body of the user (e.g., an interstitial fluid glucose level) and a target (or reference) value for that physiological condition. In a predictive operating mode, the dosage commands may be influenced by a predicted value (or anticipated measurement) for that physiological condition in the body of the user at some point in the future. Conversely, in an open-loop operating mode, the dosage commands may be configured to implement a predetermined delivery rate substantially independent of the current or predicted measurements of the physiological condition of the user.

As described in greater detail below primarily in the context of FIG. 8, in one or more exemplary embodiments, one or more diagnostic checks are performed prior to when an operating mode is entered to determine whether or not the operating mode will be viable at the expected time of entry. In this regard, various operating modes may require a particular amount of historical delivery data, measurement data, calibration data, or the like in order to calculate control parameters for implementing the operating mode. Accordingly, the diagnostic checks verify or otherwise confirm the required information is available for calculating the control parameter for implementing a subsequent instance of the operating mode. Additionally, the diagnostic checks may verify or otherwise confirm the operational status of various physical components of the infusion device to ensure those components are unlikely to be the root cause of any user alerts generated when the operating mode is implemented. For example, physical diagnostic checks may verify the remaining amount of battery life, the remaining amount of fluid in the reservoir, the amount of life remaining on the sensor(s), and the like are sufficient to last throughout the anticipated duration of the next instance of the operating mode.

In exemplary embodiments, operational information (e.g., start time, duration, and the like) pertaining to one or more prior instances of the operating mode is utilized to determine a time for when the diagnostic check(s) should be performed prior to an anticipated subsequent instance of the operating mode. At that diagnosis time in advance of the expected start time, various physical and algorithmic diagnostic checks are automatically performed to determine the viability of reinitiating or reentering the operating mode at that expected start time. The diagnostic checks determine the viability based at least in part on status information pertaining to the current and/or previous operation of the infusion device. This status information may include clinical status information or data for the patient (e.g., historical delivery data, reference measurement data, sensor measurement data, sensor calibration data, and the like) along with physical status information for the infusion device or other components of the infusion system (e.g., current battery level for the infusion device and/or sensor(s), current reservoir fluid level, and the like). When it is determined that a subsequent instance of the operating mode is not likely to be viable at the expected start time based on the currently available status information, an alert or user notification is automatically generated and provided to the user. The user notification indicates one or more recommended remedial actions that may be undertaken by the user to improve the future viability of the operating mode. In this manner, the user may engage in remedial actions in advance of the expected start time to increase the likelihood if not ensure that the operating mode will be viable by the time the user would like to reenter the operating mode. Additionally, remedial actions may also increase the likelihood if not ensure that the operating mode can be implemented for an anticipated duration without generating additional alerts that could otherwise require action by the user while in the operating mode. Thus, the overall user experience is improved by increasing the likelihood that the operating mode will be available when the user would like to enter the operating mode, while also decreasing the likelihood of the user being disturbed by additional alerts once the infusion device is implementing that operating mode.

As described in greater detail below primarily in the context of FIGS. 9-10, in exemplary embodiments, transitions between operating modes implemented by the infusion device are also supervised or otherwise managed to maintain satisfactory control of the user's physiological condition and ensure compliance with applicable delivery control rules. The delivery control rules may be dictated by regulatory requirements, manufacturer requirements, device settings, user preferences, or the like. In this regard, the destination operating mode is initialized using operational information pertaining to the current operation of the infusion device in the initial operating mode being transitioned from to provide a relatively seamless transition between operating modes. In exemplary embodiments, before transitioning to the destination operating mode, information pertaining to the operating mode currently being implemented is obtained. The operational information characterizes the current instance of the current operating mode and may include, for example, delivery or suspension information (e.g., whether or not delivery was suspended at any time, the duration delivery was suspended, and the like), the values of any active timers (e.g., the duration of a current instance of delivery suspension, the duration of a current refractory period, and the like), alert information (e.g., whether or not any alerts where generated, and information identifying what types of alerts were generated or the root cause) and information indicating why the current instance of the current operating mode is being exited. At least a portion of the operational information is provided to the destination operating mode upon the transition from the previous operating mode, with the operation of the infusion device in accordance with the destination operating mode being influenced by that operational information. For example, the destination operating mode may be initialized with the same timer values or counter values from the preceding operating mode to ensure that no time constraints or other applicable maximum limits are violated by the destination operating mode.

In exemplary embodiments, before transitioning into a destination operating mode, clinical status information pertaining to the physiological condition of the user is also obtained. As described above, the clinical information may include, for example, recent or historical sensor measurement values of the physiological condition of the user, reference measurement values of the physiological condition of the user, sensor calibration history for the user, and the like. In one or more embodiments, the destination operating mode is automatically determined based at least in part on portions of the clinical information and the operational information for the current operating mode along with the device settings or user preferences establishing a hierarchical order for the operating modes. In this regard, the clinical information and/or the operational information may be used to identify and exclude operating modes that are likely to violate any applicable constraints or requirements upon entry, with the hierarchical information for the operating modes being used to select the most preferable operating mode from among the remaining potential operating modes.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
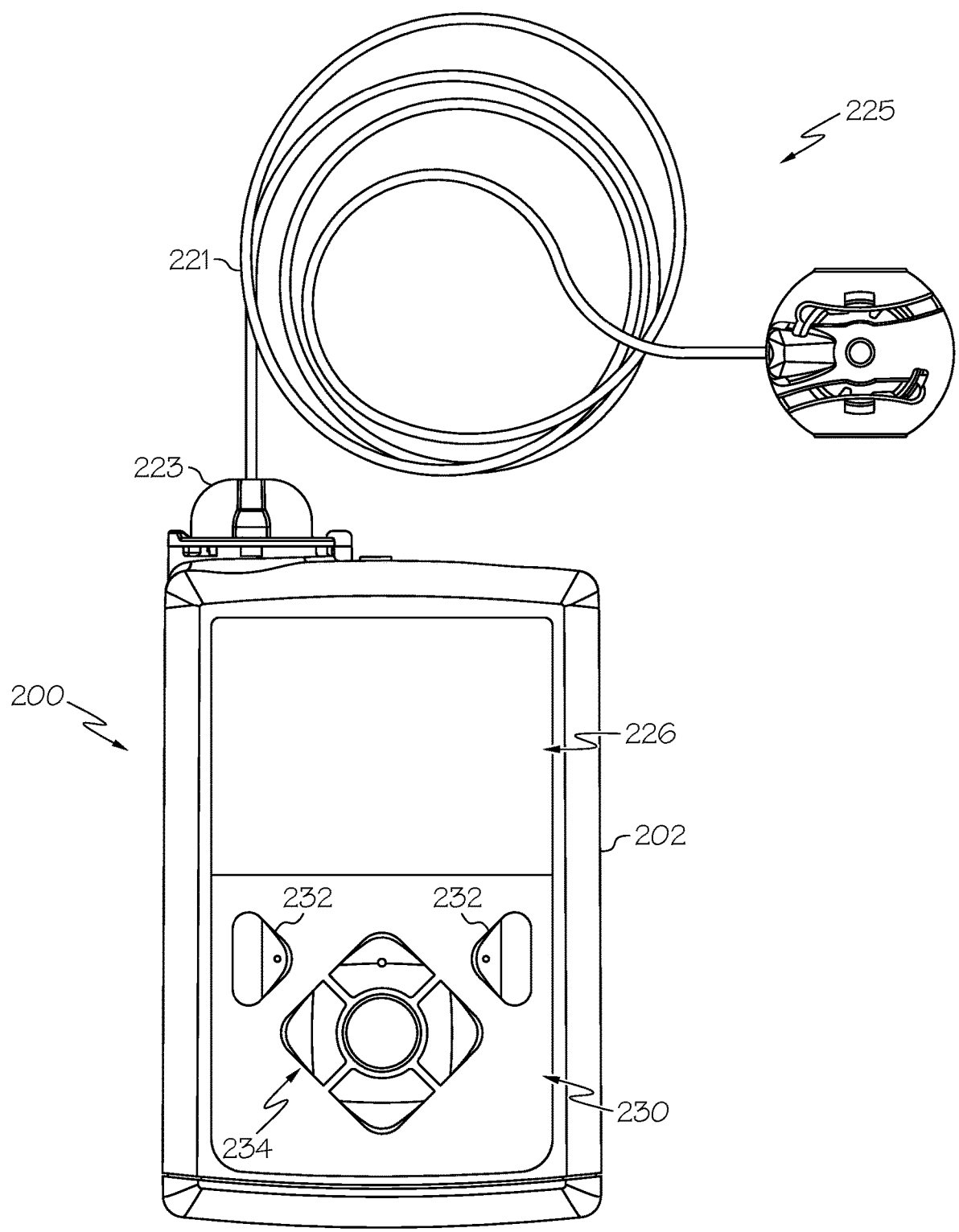
FIG. 2 depicts a plan view of an exemplary embodiment of a fluid infusion device suitable for use in the infusion system of FIG. 1.
Figure 3:
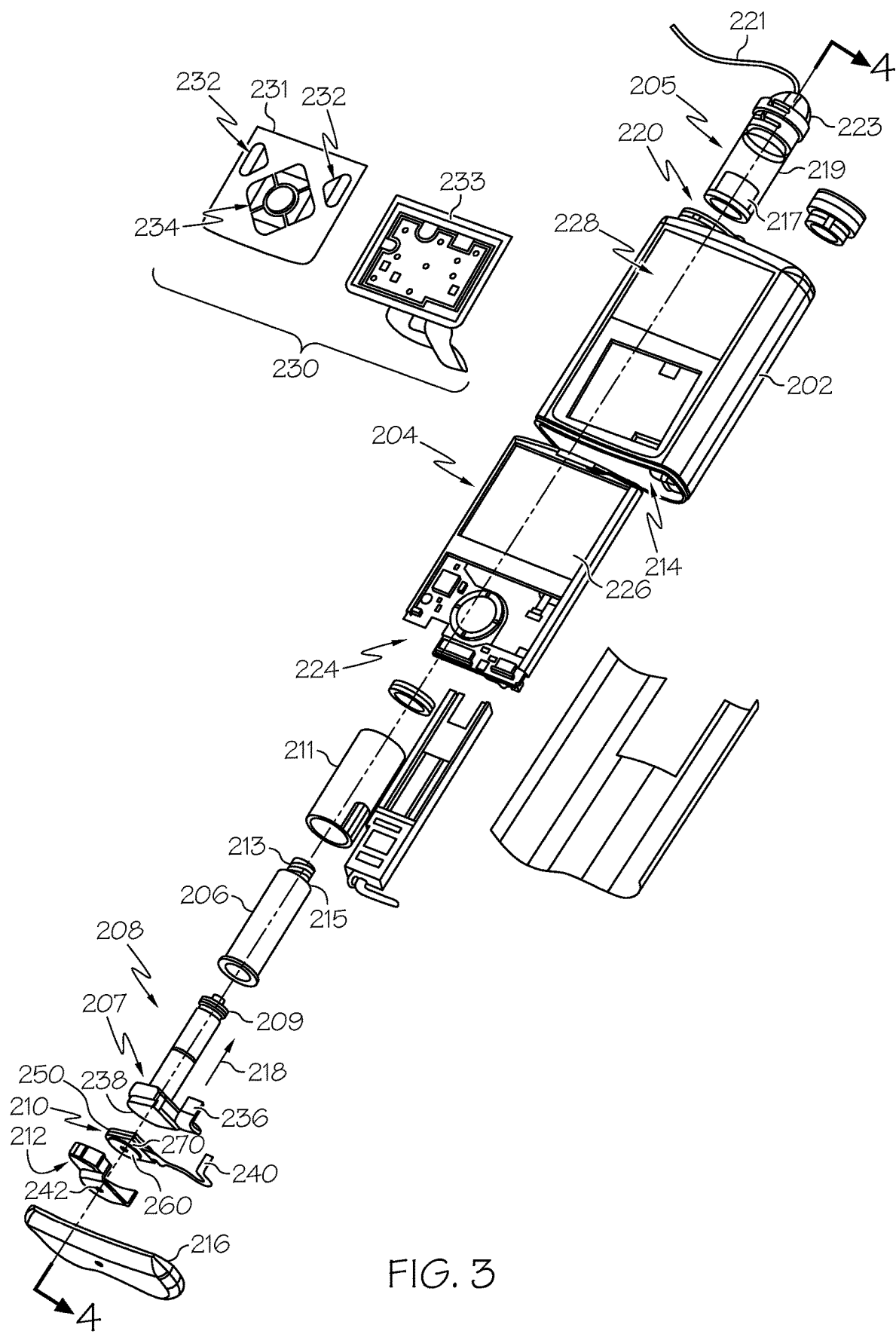
FIG. 3 is an exploded perspective view of the fluid infusion device of FIG. 2.
Figure 4:
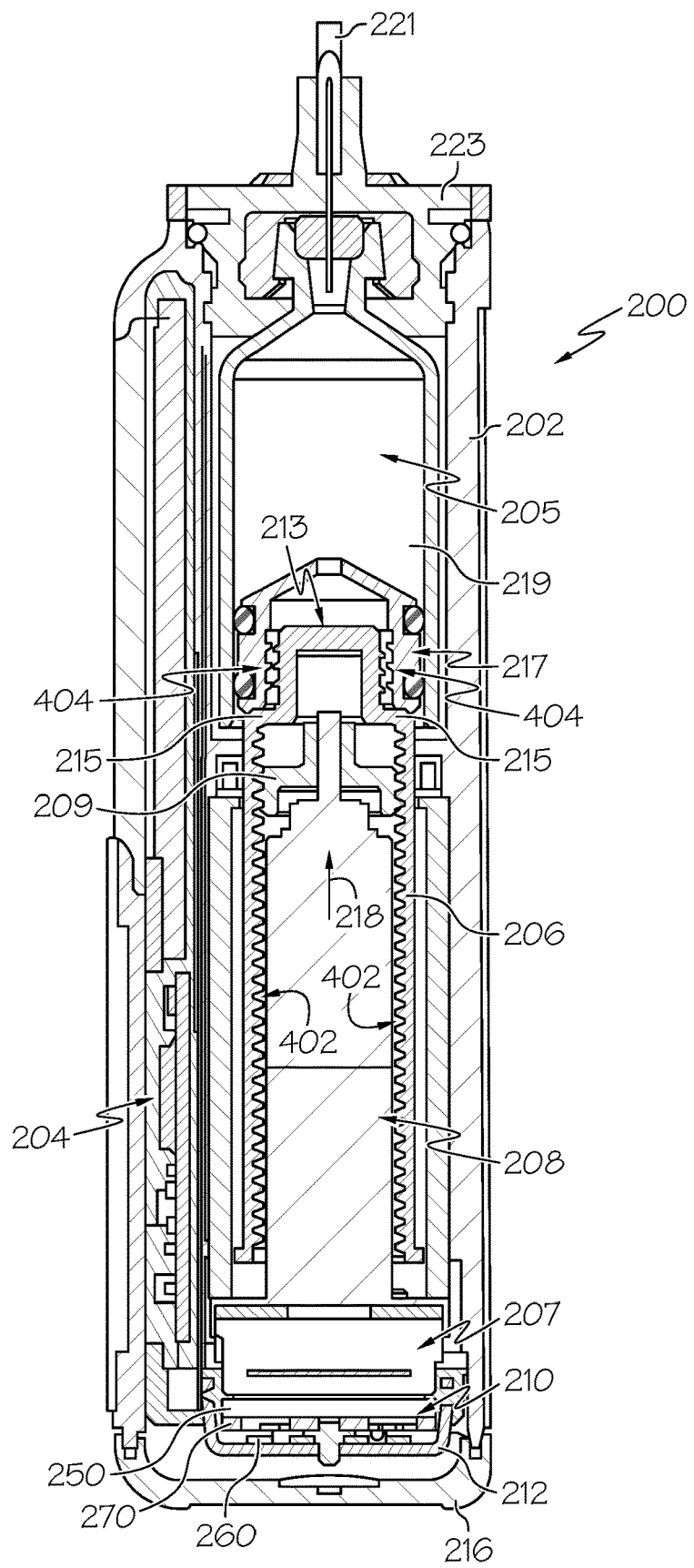
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user.

The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
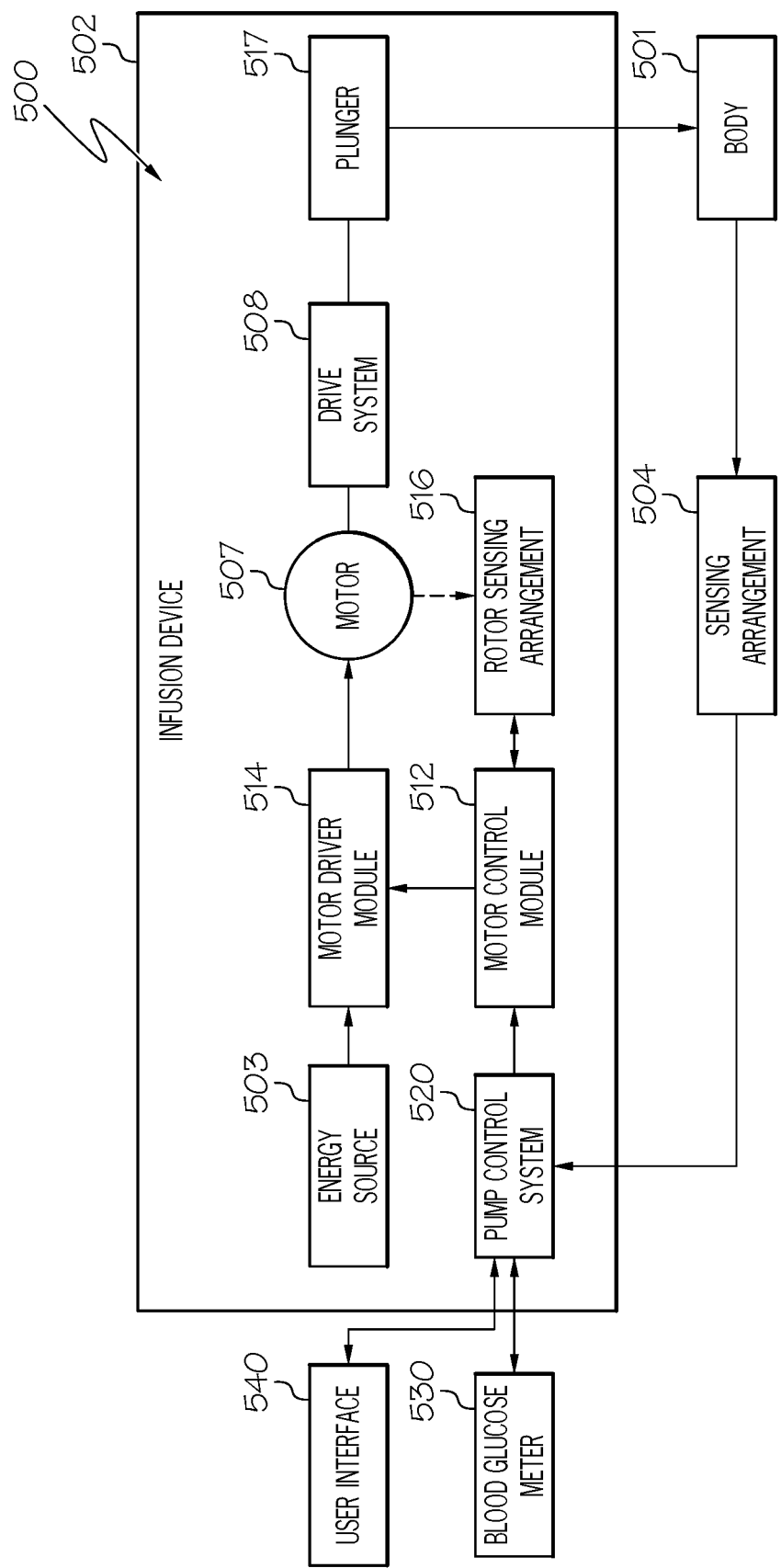
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is configured to control or otherwise regulate a physiological condition in the body 501 of a user. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose measurement value. For purposes of explanation, sensor glucose value, sensed glucose value, or variants thereof should be understood to encompass any glucose value indicative of a current glucose level in the body of the user that is based on the electrical signals output by the sensing element(s) of the sensing arrangement 504.

The pump control system 520 generally represents the electronics and other components of the infusion device 502 that control operation of the fluid infusion device 502 according to a desired infusion delivery program in a manner that may be influenced by the sensed glucose value indicative of a current glucose level in the body 501 of the user. The particular operating mode being implemented by the pump control system 520 influences the generated dosage commands for operating the motor 507 to displace the plunger 517 and deliver insulin to the body 501 of the user. For example, in a closed-loop (CL) operating mode, the pump control system 520 generates or otherwise determines dosage commands for operating the motor 507 based on the difference between a sensed glucose value and the target (or commanded) glucose value to regulate the sensed glucose value to the target. In other operating modes, the pump control system 520 may generate or otherwise determine dosage commands configured to maintain the sensed glucose value below an upper glucose limit, above a lower glucose limit, or otherwise within a desired range of glucose values. For example, in a predictive low glucose management (PLGM) operating mode, the pump control system 520 calculates or otherwise determines a predicted glucose value based on the currently sensed glucose value, and generates dosage commands configured to provide a basal infusion rate when the predicted glucose value is greater than a predictive suspend threshold and automatically suspends delivery (e.g., by providing dosage commands equal to zero) when the predicted glucose value is less than the predictive suspend threshold. In a low glucose suspend (LGS) operating mode, the pump control system 520 generates dosage commands configured to provide a basal infusion rate when the sensed glucose value is greater than a suspend threshold (which may be different from the predictive suspend threshold) and automatically suspends delivery when the sensed glucose value is less than the suspend threshold. In an open-loop (OL) operating mode, the pump control system 520 generates dosage commands configured to provide a predetermined open-loop basal infusion rate independent of the sensed glucose value. In practice, the infusion device 502 may store or otherwise maintain the target value, suspension threshold values, and/or other glucose threshold value(s) in a data storage element accessible to the pump control system 520.

The target glucose value and other threshold values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

In exemplary embodiments, the pump control system 520 includes or otherwise accesses a data storage element, memory, or other non-transitory computer-readable medium capable of storing programming instructions for execution by the pump control system 520. The computer-executable programming instructions, when read and executed, cause the pump control system 520 to determine dosage commands in accordance with a particular operating mode and perform various additional tasks, operations, functions, and processes described herein in the context of FIGS. 7-10.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 512, or in any practical combination thereof. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may be implemented by or otherwise integrated into the pump control system 520, or vice versa. Similarly, in practice, the features and/or functionality of the motor control module 512 may be implemented by or otherwise integrated into the pump control system 520, or vice versa. Furthermore, the features and/or functionality of the pump control system 520 may be implemented by control electronics 224 located in the fluid infusion device 200, while in alternative embodiments, the pump control system 520 may be implemented by a remote computing device that is physically distinct and/or separate from the infusion device 502, such as, for example, the CCD 106 or the computing device 108.

Figure 6:
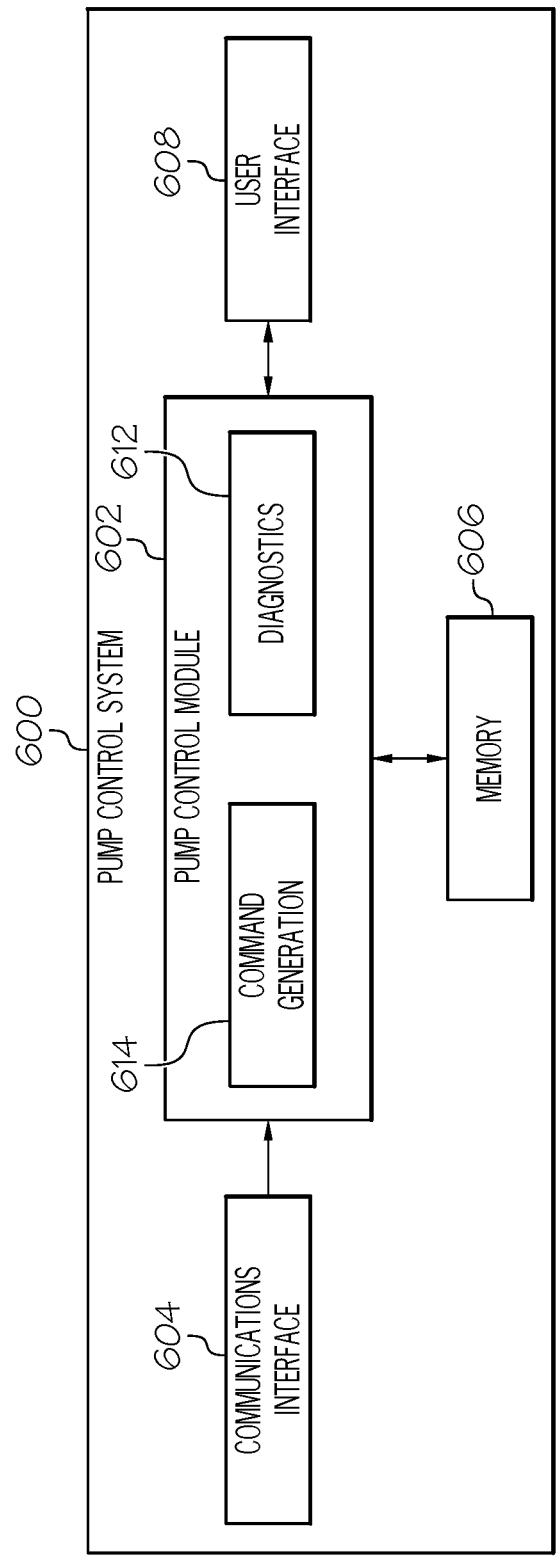
FIG. 6 is a block diagram of an exemplary pump control system suitable for use in the control system of FIG. 5.

FIG. 6 depicts an exemplary embodiment of a pump control system 600 suitable for use as the pump control system 520 in FIG. 5 in accordance with one or more embodiments. The illustrated pump control system 600 includes, without limitation, a pump control module 602, a communications interface 604, and a data storage element (or memory) 606. The pump control module 602 is coupled to the communications interface 604 and the memory 606, and the pump control module 602 is suitably configured to support the operations, tasks, and/or processes described herein. In exemplary embodiments, the pump control module 602 is also coupled to one or more user interface elements 608 (e.g., user interface 230, 540) for receiving bolus or other delivery instructions and providing notifications or other information to the user. Although FIG. 6 depicts the user interface element 608 as being integrated with the pump control system 600 (e.g., as part of the infusion device 200, 502), in various alternative embodiments, the user interface element 608 may be integrated with the sensing arrangement 504 or another element of an infusion system 100 (e.g., the computer 108 or CCD 106).

Referring to FIG. 6 and with reference to FIG. 5, the communications interface 604 generally represents the hardware, circuitry, logic, firmware and/or other components of the pump control system 600 that are coupled to the pump control module 602 and configured to support communications between the pump control system 600 and the sensing arrangement 504. In this regard, the communications interface 604 may include or otherwise be coupled to one or more transceiver modules capable of supporting wireless communications between the pump control system 520, 600 and the sensing arrangement 504 or another electronic device 106, 108 in an infusion system 100. In other embodiments, the communications interface 604 may be configured to support wired communications to/from the sensing arrangement 504.

The pump control module 602 generally represents the hardware, circuitry, logic, firmware and/or other component of the pump control system 600 that is coupled to the communications interface 604 and configured to determine dosage commands for operating the motor 507 to deliver fluid to the body 501 based on data received from the sensing arrangement 504 and perform various additional tasks, operations, functions and/or operations described herein. For example, in exemplary embodiments, pump control module 602 implements or otherwise executes a command generation module 614 that automatically calculates or otherwise determines a dosage command for operating the motor 507 of the infusion device 502 in accordance with a particular operating mode. In exemplary embodiments described herein, the command generation module 614 supports multiple different operating modes having different delivery control schemes associated therewith. Additionally, the command generation module 614 may generate dosage commands for delivering boluses that are manually-initiated or otherwise instructed by a user via a user interface element 608. The illustrated pump control module 602 also implements or otherwise executes a diagnostics module 612 that generates or otherwise provides user notifications or alerts via a user interface element 608. As described in greater detail below in the context of FIG. 8, in exemplary embodiments, the diagnostics module 612 determines the viability of a particular operating mode in advance of a subsequent instance of that operating mode and generates notifications via the user interface element 608 that indicate recommended remedial actions to improve the viability of that operating mode.

Still referring to FIG. 6, depending on the embodiment, the pump control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 602, or in any practical combination thereof. In exemplary embodiments, the pump control module 602 includes or otherwise accesses the data storage element or memory 606, which may be realized using any sort of non-transitory computer-readable medium capable of storing programming instructions for execution by the pump control module 602. The computer-executable programming instructions, when read and executed by the pump control module 602, cause the pump control module 602 to perform the tasks, operations, functions, and processes described in greater detail below.

It should be understood that FIG. 6 is a simplified representation of a pump control system 600 for purposes of explanation and is not intended to limit the subject matter described herein in any way. For example, in some embodiments, the features and/or functionality of the motor control module 512 may be implemented by or otherwise integrated into the pump control system 600 and/or the pump control module 602, for example, by the command generation module 614 converting the dosage command into a corresponding motor command, in which case, the separate motor control module 512 may be absent from an embodiment of the infusion device 502.

Figure 7:
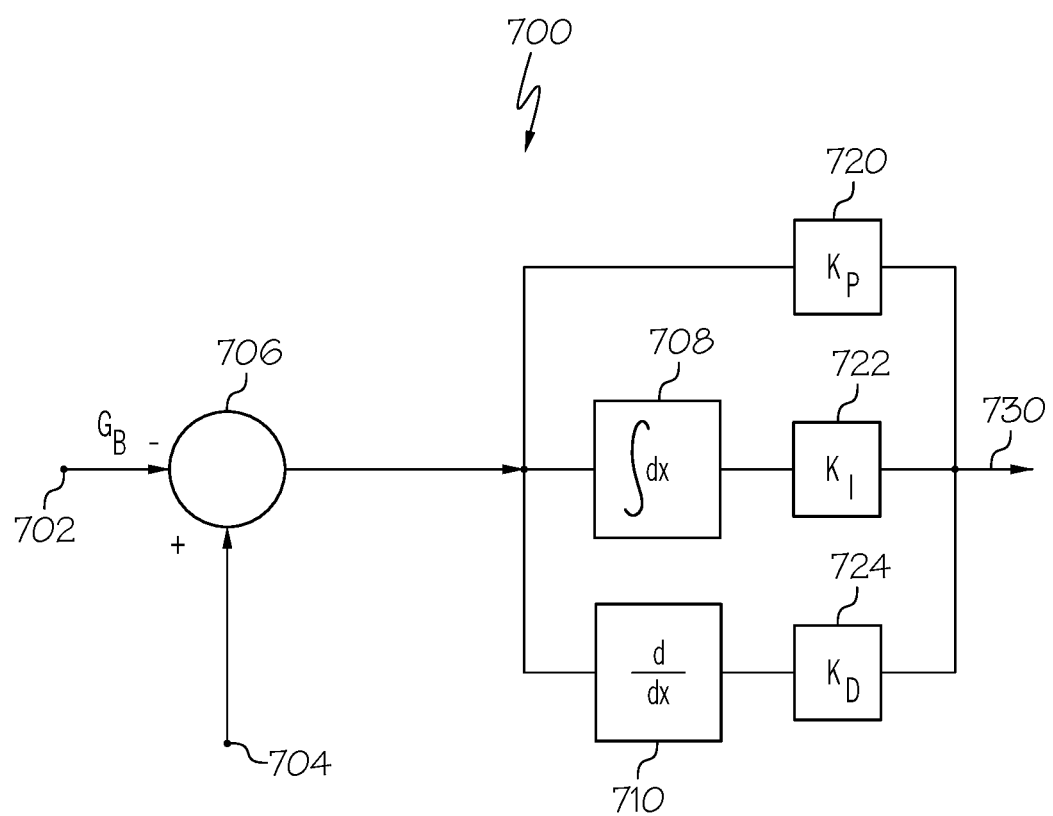
FIG. 7 is a block diagram of a closed-loop control system that may be implemented or otherwise supported by the pump control system in the fluid infusion device of FIG. 5 in one or more exemplary embodiments.

FIG. 7 depicts an exemplary closed-loop control system 700 that may be implemented by a pump control system 520, 600 to regulate a condition in the body of a user to a desired (or target) value. It should be appreciated that FIG. 7 is a simplified representation of the control system 700 for purposes of explanation and is not intended to limit the subject matter described herein in any way.

In exemplary embodiments, the control system 700 receives or otherwise obtains a target glucose value at input 702. In some embodiments, the target glucose value may be stored or otherwise maintained by the infusion device 502 (e.g., in memory 606), however, in some alternative embodiments, the target value may be received from an external component (e.g., CCD 106 and/or computer 108). In one or more embodiments, the target glucose value may be dynamically calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 700 also receives or otherwise obtains a current glucose measurement value from the sensing arrangement 504 at input 704. The illustrated control system 700 implements or otherwise provides proportional-integral-derivative (PID) control to determine or otherwise generate delivery commands for operating the motor 507 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 702 and the measured glucose level at input 704 to generate or otherwise determine a dosage (or delivery) command provided at output 730. Based on that delivery command, the motor control module 512 operates the motor 507 to deliver insulin to the body of the user to influence the user's glucose level, and thereby reduce the difference between a subsequently measured glucose level and the target glucose level.

The illustrated control system 700 includes or otherwise implements a summation block 706 configured to determine a difference between the target value obtained at input 702 and the measured value obtained from the sensing arrangement 504 at input 704, for example, by subtracting the target value from the measured value. The output of the summation block 706 represents the difference between the measured and target values, which is then provided to each of a proportional term path, an integral term path, and a derivative term path. The proportional term path includes a gain block 720 that multiplies the difference by a proportional gain coefficient, $K_P$, to obtain the proportional term. The integral term path includes an integration block 708 that integrates the difference and a gain block 722 that multiplies the integrated difference by an integral gain coefficient, $K_I$, to obtain the integral term. The derivative term path includes a derivative block 710 that determines the derivative of the difference and a gain block 724 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 730. Various implementation details pertaining to closed-loop PID control and determine gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 502. The PID gain coefficients may be maintained by the memory 606 accessible to the pump control module 602. In this regard, the memory 606 may include a plurality of registers associated with the control parameters for the PID control. For example, a first parameter register may store the target glucose value and be accessed by or otherwise coupled to the summation block 706 at input 702, and similarly, a second parameter register accessed by the proportional gain block 720 may store the proportional gain coefficient, a third parameter register accessed by the integration gain block 722 may store the integration gain coefficient, and a fourth parameter register accessed by the derivative gain block 724 may store the derivative gain coefficient.

Figure 8:
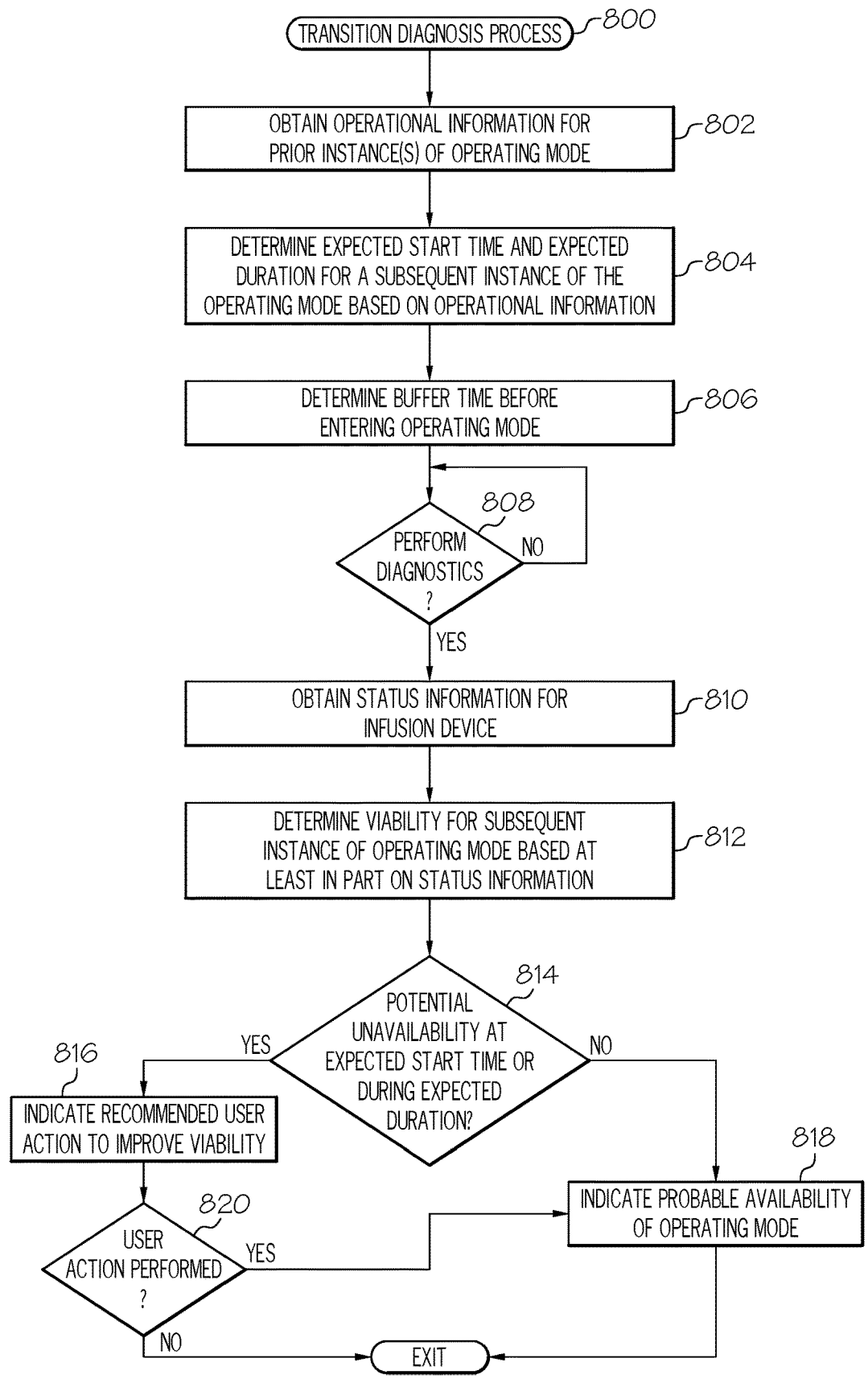
FIG. 8 is a flow diagram of an exemplary transition diagnosis process suitable for use with the control system of FIG. 5.

FIG. 8 depicts an exemplary transition diagnosis process 800 suitable for implementation by a control system associated with a fluid infusion device to determine whether transitioning into a particular operating mode at some subsequent time is viable. For purposes of explanation, the transition diagnosis process 800 may be described herein in the context of a closed-loop operating mode, however, it will be appreciated that the subject matter described herein is not limited to the particular destination operating mode being diagnosed. Various tasks performed in connection with the transition diagnosis process 800 may be performed by hardware, firmware, software executed by processing circuitry, or any combination thereof. For illustrative purposes, the following description refers to elements mentioned above in connection with FIGS. 1-7. In practice, portions of the transition diagnosis process 800 may be performed by different elements of the control system 500, such as, for example, the infusion device 502, the pump control system 520, 600, the diagnostics module 612, the command generation module 614 and/or the user interface 540, 608. It should be appreciated that the transition diagnosis process 800 may include any number of additional or alternative tasks, the tasks need not be performed in the illustrated order and/or the tasks may be performed concurrently, and/or the transition diagnosis process 800 may be incorporated into a more comprehensive procedure or process having additional functionality not described in detail herein. Moreover, one or more of the tasks shown and described in the context of FIG. 8 could be omitted from a practical embodiment of the transition diagnosis process 800 as long as the intended overall functionality remains intact.

In the illustrated embodiment, the transition diagnosis process 800 initializes or otherwise begins by obtaining operational information pertaining to one or more prior instances of the operating mode being analyzed and calculates or otherwise determines an expected start time and an expected duration of the next subsequent instance of the operating mode based on the operational information for the prior instances (tasks 802, 804). In this regard, the pump control system 520, 600 may store or otherwise maintain historical information pertaining to the previous operation of the infusion device 502 that characterizes prior instances of the different operating modes supported by the pump control system 520, 600. For example, the pump control system 520 may store or otherwise maintain operational information indicative of the respective start times of prior instances of the closed-loop operating mode along with the respective durations (or stop times) of prior instances of the closed-loop operating mode. Based on this historical operational information maintained for the closed-loop operating mode, the pump control system 520, 600 and/or diagnostics module 612 may determine an expected (or anticipated) start time for a subsequent instance of the closed-loop operating mode along with an expected duration for the subsequent instance of the closed-loop operating mode. For example, the expected start time may be calculated by averaging the individual start times for preceding instances of the closed-loop operating mode, and the expected duration may be calculated by averaging the respective durations of preceding instances of the closed-loop operating mode.

In exemplary embodiments, the transition diagnosis process 800 calculates or otherwise determines a buffer time before the subsequent instance of the destination operating mode is expected to be initiated (task 806). The buffer time represents the amount of time in advance of the expected start time for analyzing the future viability of entering the destination operating mode at the expected start time. In exemplary embodiments, the buffer time is determined so that it provides sufficient time for remedial actions to be undertaken to improve the viability the destination operating mode by the expected start time. For example, calculating the PID control parameters for the closed-loop operating mode may require a certain amount of reference blood glucose measurements, sensor measurement data, insulin delivery information, or the like. Accordingly, when the destination operating mode is the closed-loop operating mode, the buffer time is chosen to provide enough time between the diagnostics checks and the expected start time for the next instance of the closed-loop operating mode to allow the required amount of data for calculating the PID control parameters to be obtained by the expected start time. In this regard, the buffer time may vary depending on the particular destination operating mode being analyzed and the respective algorithmic diagnostic checks to be performed for that particular operating mode. For example, the buffer time for the closed-loop operating mode may be greater than the buffer time for a LGS operating mode due to the calculation of the closed-loop PID control parameters requiring a greater amount of underlying data than the LGS operating mode control parameters. In one embodiment, a five hour buffer time is utilized for the closed-loop operating mode to ensure historical delivery information sufficient for calculating patient-specific control parameters will likely exist at the expected start time for the closed-loop operating mode.

Additionally, the buffer time may vary dynamically depending on the iteration of the diagnosis process 800. For example, if previous iterations of the diagnosis process 800 have already determined that aspects of the destination operating mode that require a longer buffer time are unlikely to impact the future viability of the operating mode (e.g., sufficient historical data is available), the buffer time may be reduced for subsequent iterations of the diagnosis process 800. In one or more embodiments, where the diagnostics module 612 analyzes the viability of the sensing arrangement 504 as part of determining the viability for the next instance of the destination operating mode, the buffer time is determined to be greater than or equal to a minimum amount of time required to calibrate the sensing arrangement 504. In this regard, if a reliability or accuracy metric associated with the sensing arrangement 504 indicates a sensing element should be replaced, the buffer time ensures that there will be enough time to calibrate the sensing arrangement 504 with a new sensing element before the expected start time. In one embodiment, a minimum buffer time of two hours may be implemented.

The diagnosis process 800 continues by automatically identifying or otherwise determining when to begin analyzing the viability of the destination operating mode based on the buffer time and the expected start time (task 808). In this regard, at the buffer time before the expected start time, the diagnosis process 800 obtains status information for the operation of the infusion device and calculates or otherwise determines viability of a subsequent instance of the operating mode based at least in part on that status information (tasks 810, 812). When one or more of the physical or algorithmic diagnostics checks indicates the destination operating mode is unlikely to be viable at the expected start time for the expected duration, the diagnosis process 800 automatically generates or otherwise provides one or more user notifications indicative of recommended remedial actions for improving the future viability of the operating mode (tasks 814, 816). In this regard, the diagnostics module 612 operates a user interface 540, 608 to provide indication of a remedial action that the user can perform to increase the likelihood that the operating mode will be viable at the expected start time.

In exemplary embodiments, the diagnostics module 612 automatically obtains clinical and physical status information pertaining to the current and/or previous operation of the infusion device 502 from the memory 606, such as, historical delivery data (e.g., timing and amounts of correction boluses, daily insulin delivered, etc.), blood glucose reference measurement data (e.g., measurement values obtained from blood glucose meter 530 and the corresponding times of measurement), sensor calibration data (e.g., current and/or previous calibration factors), recent sensor measurement data, the current status of the energy source 503 (e.g., the current battery level), the current amount of fluid remaining in the reservoir, and the like. The diagnostics module 612 analyzes the status information and determines the viability of the destination operating mode for the expected duration of the next instance of the destination operating mode. When one or more aspects of the status information fail to satisfy a respective viability criterion, the diagnostics module 612 determines that the operating mode is unlikely to be viable at the expected start time for the expected duration.

In exemplary embodiments, the diagnostics module 612 determines whether implementing the destination operating mode at the expected start time for the expected duration is viable from a physical perspective. In this regard, the diagnostics module 612 performs a number of physical diagnostics checks to verify the infusion device 502 is physically capable of implementing the destination operating mode at the expected start time for the expected duration. For example, the diagnostics module 612 may calculate or otherwise determine an expected amount of power consumption for the infusion device 502 over the sum of the remaining buffer time before the expected start time and the expected duration, and identifies or otherwise determines the infusion device 502 is not viable for the destination operating mode when the current battery level is less than the expected amount of power consumption. In this regard, the diagnostics module 612 effectively determines whether a low battery alert that could disrupt or otherwise degrade the user experience is likely to be generated by the infusion device 502 during the expected duration of the destination operating mode.

Similarly, the diagnostics module 612 may calculate an expected amount of insulin that will be delivered by the infusion device 502 over the sum of the remaining buffer time before the expected start time and the expected duration based on the historical delivery data and the user's recent sensor glucose measurement value(s), and determines the infusion device 502 is not viable for the destination operating mode when the current amount of insulin remaining is less than the expected amount of insulin to be delivered. Thus, the diagnostics module 612 effectively determines whether a low fluid alert is likely to be generated by the infusion device 502 at some point during the expected duration of the destination operating mode. The diagnostics module 612 may also determine whether any other critical alerts are likely to be generated during the expected duration or whether any events or conditions are likely to occur that would result in the destination operating mode automatically being terminated during the expected duration. In such embodiments, the diagnostics module 612 determines the infusion device 502 is not viable for the destination operating mode when it is determined that a critical alert (or alternatively, a number of alerts exceeding a maximum alert threshold) or an automatic exit event is likely to occur during the expected duration.

In one or more embodiments, the diagnostics module 612 may also calculate or otherwise determine the viability of the sensing arrangement 504 for the expected duration. For example, the diagnostics module 612 may calculate or otherwise determine one or more reliability or accuracy metrics associated with the sensing arrangement 504 based on recent sensor measurement values, blood glucose reference measurement values and/or other calibration information. The diagnostics module 612 determines a projected reliability or accuracy metrics during the expected duration, and identifies or otherwise determines the sensing arrangement 504 is not viable for the destination operating mode when the value of a projected metric is less than a replacement threshold value at any point during the expected duration. In this regard, the diagnostics module 612 effectively determines whether a replace sensor alert that could disrupt or otherwise degrade the user experience is likely to be generated by the infusion device 502 at some point during the expected duration. In other embodiments, the diagnostics module 612 may determine the sensing arrangement 504 is not viable for the destination operating mode if a difference between the current sensor glucose measurement value and a predicted glucose value is greater than a threshold value, a calibration factor for the sensing arrangement 504 will have expired by the expected start time, communications with the sensing arrangement 504 are deteriorating (e.g., based on an increasing number or frequency of dropouts in communications over a preceding time interval), a difference between the current calibration factor and the preceding calibration factor is greater than a threshold amount (e.g., a difference of more than 35%), or a difference between reference blood glucose measurement value and the corresponding sensor measurement value used for the current calibration factor is greater than a threshold amount (e.g., the sensor measurement value is more than 35% greater than or less than the reference blood glucose measurement value). Additionally, in some embodiments, the diagnostics module 612 may obtain a current battery level for the sensing arrangement 504, determine an expected amount of power consumption for the sensing arrangement 504 over the sum of the remaining buffer time before the expected start time and the expected duration, and determine the sensing arrangement 504 is not viable when its current battery level is less than that expected amount of power consumption.

Additionally, the diagnostics module 612 performs a number of algorithmic diagnostics checks to determine the availability of the destination operating mode at the expected start time. In this regard, the diagnostics module 612 determines the destination operating mode is likely to be unavailable if one or more control parameters relied on by the delivery control scheme of the destination operating mode cannot be calculated, determined, or otherwise obtained at the expected start time. Thus, if insufficient data exists for calculating a particular control parameter, the diagnostics module 612 may determine that the destination operating mode is likely to be unavailable, and therefore not viable. For example, in one embodiment, the closed-loop operating mode utilizes a maximum output insulin infusion rate (U/hr) that is calculated based on the user's total daily insulin dose. When the diagnostics module 612 determines that the less than two consecutive preceding days total daily insulin dose information exists, the diagnostics module 612 determines that the closed-loop operating mode likely will not be viable at the expected start time without a valid maximum output insulin infusion rate. In such situations, the diagnostics module 612 may generate a user notification to manually input a maximum output insulin infusion rate (or alternatively, a total daily insulin dose). Thus, if the user would like to implement the closed-loop operating mode at a subsequent time but is unsure of how to proceed, the user may contact his or her doctor or other healthcare provider for assistance in determining the maximum output insulin infusion rate (or total daily insulin dose) that is most likely to suit the user's individual needs and insulin response.

In exemplary embodiments, the diagnostics module 612 also determines whether the control parameters will be valid for the entirety of the expected duration of the next instance of the operating mode, and the diagnostics module 612 determines the destination operating mode is not likely to be viable if a control parameter relied on by the delivery control scheme is likely to become invalid at some point during the expected duration. For example, the diagnostics module 612 may determine an infusion rate calculated based on predicted sensor glucose values will be invalid during the expected duration based on the expected rate or frequency of communications dropouts between the infusion device 502 and the sensing arrangement 504.

In the case of a physical diagnostics check indicating the implementation of the operating mode may not be viable for the expected duration, the diagnostics module 612 recommends actions that the user can perform to help ensure the infusion device 502 and the sensing arrangement 504 will be physically capable of implementing the operating mode for the expected duration by the expected start time. For example, when the diagnostics module 612 determines the energy source 503 will likely be unable to provide the expected amount of power consumption by the infusion device 502 throughout the buffer time and the expected duration, the diagnostics module 612 may generate or otherwise provide an indication on a display device 540, 608 that recommends the user recharge or replace the energy source 503. Thus, in advance of the expected start time, the user may initiate replenishment of the energy source 503 so that its state of charge (or power capability) at the expected start time exceeds the expected power consumption over the expected duration. Similarly, when the diagnostics module 612 determines the fluid level of the reservoir is likely too low to provide the expected amount of insulin that will need to be delivered over the buffer time and the expected duration, the diagnostics module 612 may generate or otherwise provide an indication on a display device 540, 608 that recommends the user refill or replace the fluid reservoir. Thus, in advance of the expected start time, the user may replenish the reservoir of the infusion device 502 so that the amount of insulin onboard the infusion device 502 at the expected start time exceeds the expected insulin delivery over the expected duration. Likewise, when the diagnostics module 612 determines the sensing arrangement 504 is likely to require replacement, recalibration, or recharging, the diagnostics module 612 may generate or otherwise provide the appropriate notification to the user so that the user may recharge the sensing arrangement 504, replace the sensing element of the sensing arrangement 504, recalibrate the sensing arrangement 504, or the like.

Likewise, in the case of an algorithmic diagnostics check indicating the implementation of the operating mode may not be viable, the diagnostics module 612 recommends actions that the user can perform to help ensure the valid control parameters for the delivery control scheme associated with the destination operating mode will be able to be calculated at the expected start time. For example, if calculating a control parameter requires a particular number of blood glucose measurement values (or a particular number of pairs of blood glucose measurement values and sensor glucose measurement values) over a preceding interval of time (e.g., the prior 12 hours) the diagnostics module 612 may generate or otherwise provide an indication to the user to obtain one or more blood glucose measurement values via the blood glucose meter 530, so that the amount of blood glucose measurement data required for calculating that control parameter will be maintained by the infusion device 502 (e.g., in memory 606) at the expected start time. In one embodiment, the diagnostics module 612 generates a notification to obtain a new blood glucose measurement value via the blood glucose meter 530 in response to determining that no reference blood glucose measurement value within 12 hours of the expected start time is currently available.

In one embodiment, algorithmic diagnostics checks to determine the availability of the destination operating mode at the expected start time based on an expected duration of operation in another operating mode (e.g., which may be the current operating mode). For example, if the user is returning from a pump vacation or other period of non-operation, it may be required that the infusion device 502 be operated in an open-loop operating mode for a minimum period of time (e.g., 5 hours) to support calculating a plasma insulin estimate and/or other patient-specific parameters at the expected start time. In this regard, the buffer time may be chosen to be greater than or equal to the minimum period of time for the open-loop operating mode, and the diagnostics module 612 may generate or otherwise provide an indication to the user to operate the infusion device 502 in the open-loop operating mode when the amount of time that the infusion device 502 has been operated in the open-loop operating mode is less than the minimum period of time. In this regard, when the infusion device 502 is currently in the open-loop operating mode but has not been operated for the minimum period of time, the diagnostics module 612 may calculate or otherwise determine an amount of time required to achieve the minimum period of time and generate or otherwise provide a notification to the user that indicates how much longer the user should maintain the infusion device 502 in the open-loop operating mode.

Still referring to FIG. 8, in the illustrated embodiment, when the diagnosis process 800 determines that the destination operating mode is likely to be viable at the expected start time for the expected duration, the diagnosis process 800 may also automatically generate or otherwise provides an indication of the future viability of the operating mode (task 818). For example, the diagnostics module 612 may operate a user interface 540, 608 to provide indication of the viability of the operating mode. In this regard, in situations where the destination operating mode is manually-initiated, the user is provided with a notification that lets the user know that the destination operating mode should be available to be initiated as desired. Likewise, in situations where the diagnosis process 800 determines that the user has sufficiently performed the recommended remedial action(s), the diagnosis process 800 may automatically clear or otherwise remove the notification(s) indicating the recommended remedial action(s) and provide another notification that indicates the viability of the operating mode (task 820). In this regard, the diagnostics module 612 may detect or otherwise identify when the user has initiated a remedial action, and in response, repeat the corresponding diagnostic check(s) to ensure that the remedial action has resolved any viability concerns. For example, if the diagnostics module 612 may detect or otherwise verify that the energy source 503 is sufficiently charged, the reservoir contains a sufficient amount of insulin, the sensing arrangement 504 is sufficiently charged and/or calibrated, and/or the like before automatically clearing the recommendations and providing indication that entering the operating mode is now viable. Similarly, the diagnostics module 612 may periodically analyze the historical delivery data, blood glucose measurement data, sensor calibration data, and the like maintained in memory 606 and detect or otherwise verify that all of the control parameters can be determined before automatically providing indication that the operating mode is now viable.

It should be noted that in some embodiments, after the next instance of the destination operating mode is initiated, the diagnostics module 612 may periodically perform the physical and algorithmic diagnostic checks while the operating mode is being implemented to verify the continued viability of the operating mode (e.g., tasks 810, 812, 814). In such embodiments, when the diagnostics module 612 determines that the operating mode may not be viable, the diagnostics module 612 may generate or otherwise provide the appropriate recommendations to the user (e.g., task 816) so that the user may improve the future viability of the operating mode before any critical alerts are generated or before the operating mode must be terminated. Additionally, it should be noted that the operational information for the next instance of the destination operating mode may be stored or otherwise maintained for use in determining an updated expected start time and an updated expected duration during the next iteration of the diagnosis process 800 for the next subsequent instance of the operating mode (e.g., tasks 802, 804). In this regard, the expected start time, the expected duration and/or the buffer time may vary dynamically during operation of the infusion device 502 to adapt to changes in the user's usage of the particular operating mode.

In one exemplary embodiment, the diagnosis process 800 is performed for a closed-loop operating mode that the user operates the infusion device 502 in overnight while he or she is sleeping. For example, at bedtime, the user may manipulate the user interface 540, 608 to initiate the closed-loop operating mode to regulate the user's blood glucose while the user is sleeping. In this regard, the infusion device 502 may store or otherwise maintain historical operational information for the overnight closed-loop operating mode, such as, for example, the respective starting times at which the closed-loop operating mode is initiated along with the respective durations or times at which the closed-loop operating mode is terminated (e.g., when the user wakes up in the morning or the operating mode times out). Accordingly, during the day prior to a subsequent instance of the closed-loop operating mode, the diagnostics module 612 and/or the diagnosis process 800 may calculate or otherwise determine the user's average bedtime (e.g., by averaging the respective start times of the recent instances of the operating mode) and the average duration of the operating mode (e.g., the average amount of time the user sleeps) (e.g., tasks 802, 804). Thereafter, the diagnostics module 612 and/or the diagnosis process 800 automatically performs the diagnostics checks the buffer time before the user's average bedtime (e.g., tasks 808, 810, 812) to ensure that the overnight closed-loop operating mode will be available at the time the user is likely to go to bed. For example, if the average bedtime for the user is at 10 P.M. and the buffer time is determined to be five hours, the diagnostics module 612 and/or the diagnosis process 800 automatically performs the diagnostics checks at 5 P.M. to provide notifications of recommended actions for the user to increase the viability or availability of the overnight closed-loop operating mode (e.g., obtain a new blood glucose reference measurement value, replace or recalibrate the sensing arrangement 504, and the like).

Figure 9:
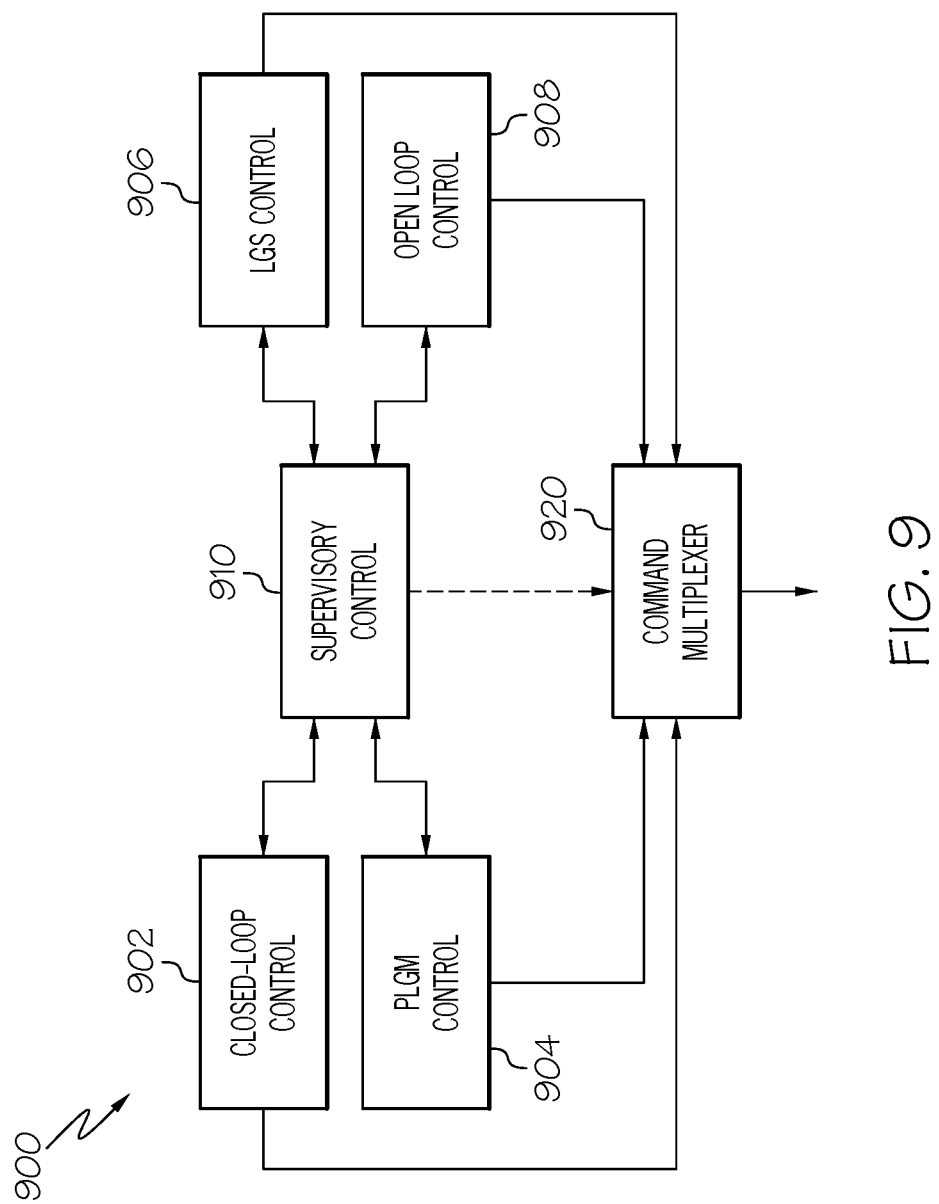
FIG. 9 is a block diagram of an exemplary management system that may be implemented or otherwise supported by the pump control system in the fluid infusion device of FIG. 5 in one or more exemplary embodiments.

Turning now to FIG. 9, in accordance with one or more embodiments, a management system 900 manages transitions between operating modes supported by an infusion device. In one or more exemplary embodiments described herein, the management system 900 is implemented by a pump control system 520, 600 and/or pump control module 602. In this regard, the various modules 902, 904, 906, 908, 910 may be subcomponents of the pump control module 602 or the command generation module 614. For example, in one embodiment, the command generation module 614 includes or otherwise implements the management system 900. The illustrated system 900 includes a plurality of operating mode control modules 902, 904, 906, 908 along with a supervisory control module 910 that manages transitions between the respective operating modes. In the illustrated embodiment, the supervisory control module 910 operates a command multiplexer 920, which is coupled to the motor control module 512 to output a dosage command from the selected operating mode control module 902, 904, 906, 908 corresponding to the operating mode currently being implemented by the infusion device 502.

The closed-loop control module 902 generally represents the components of the pump control system 520, 600 that are configured to support the closed-loop operating mode. In this regard, the closed-loop control module 902 may implement the closed-loop control system 700 of FIG. 7 and generate a dosage command based on a difference between the current (or most recent) measurement of the user's interstitial fluid glucose level and a target (or reference) interstitial fluid glucose value.

The predictive low glucose control module 904 generally represents the components of the pump control system 520, 600 that are configured to support a PLGM operating mode. As described above, the PLGM control module 904 generates dosage commands to provide a basal infusion rate when a predicted glucose value is greater than a predictive suspend threshold and automatically suspends delivery (or generates dosage commands equal to zero) when the predicted glucose value is less than the predictive suspend threshold.

The low glucose control module 906 generally represents the components of the pump control system 520, 600 that are configured to support a LGS operating mode. As described above, the LGS control module 906 by generates dosage commands to provide a basal infusion rate when the current (or most recent) measurement of the user's interstitial fluid glucose level is greater than a suspend threshold and automatically suspends delivery when the current measurement value is less than the suspend threshold.

The open-loop control module 908 generally represents the components of the pump control system 520, 600 that are configured to support an open-loop operating mode. In this regard, the open-loop control module 908 generates dosage commands configured to provide a predetermined open-loop basal infusion rate.

In the illustrated embodiment, the command multiplexer 920 is coupled to the outputs of the respective control modules 902, 904, 906, 908 to selectively output the dosage command from one of the modules 902, 904, 906, 908 to the motor control module 512 in response to a selection signal from the supervisory control module 910. In this regard, the selection signal identifies the operating mode that is currently being implemented by the infusion device 102, 200, 502. The supervisory control module 910 generally represents the components of the pump control system 520, 600 that are coupled to the control modules 902, 904, 906, 908 and configured to support the operating mode transition process 1000 and perform the tasks, operations, functions, and processes described herein managing transitions between operating modes associated with the respective control modules 902, 904, 906, 908.

It should be appreciated that FIG. 9 is a simplified representation of the management system 900 for purposes of explanation and is not intended to limit the subject matter described herein in any way. In this regard, depending on the embodiment, any number of operating mode control modules may be present to support any number of operating modes. In some embodiments, the features and/or functionality of the command multiplexer 920 may be implemented by or otherwise integrated into the supervisory control module 910. Furthermore, while in some embodiments the features and/or functionality of the management system 900 are implemented by control electronics 224 located in the fluid infusion device 200, 502, in alternative embodiments, various aspects of the management system 900 may be implemented by a remote computing device that is physically distinct and/or separate from the infusion device 200, 502, such as, for example, the CCD 106 or the computing device 108.

Figure 10:
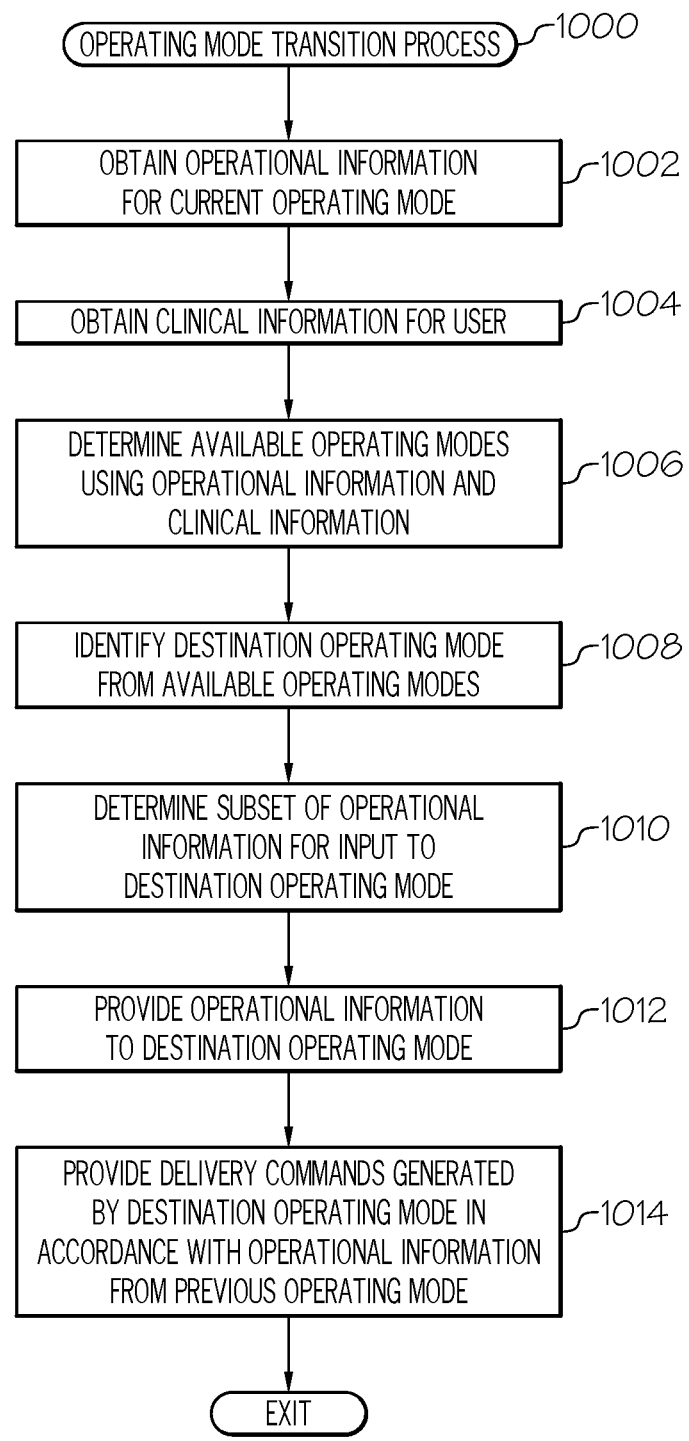
FIG. 10 is a flow diagram of an exemplary operating mode transition process suitable for use with the control system of FIG. 5.

FIG. 10 depicts an exemplary operating mode transition process 1000 suitable for implementation by a control system associated with a fluid infusion device to manage transitions between operating modes supported by the device. Various tasks performed in connection with the operating mode transition process 1000 may be performed by hardware, firmware, software executed by processing circuitry, or any combination thereof. For illustrative purposes, the following description refers to elements mentioned above in connection with FIGS. 1-7. In practice, portions of the operating mode transition process 1000 may be performed by different elements of the control system 500, such as, for example, the infusion device 502, the pump control system 520, 600, the diagnostics module 612, the command generation module 614, the management system 900, the supervisory control module 910 and/or the command multiplexer 920. It should be appreciated that the operating mode transition process 1000 may include any number of additional or alternative tasks, the tasks need not be performed in the illustrated order and/or the tasks may be performed concurrently, and/or the operating mode transition process 1000 may be incorporated into a more comprehensive procedure or process having additional functionality not described in detail herein. Moreover, one or more of the tasks shown and described in the context of FIG. 10 could be omitted from a practical embodiment of the operating mode transition process 1000 as long as the intended overall functionality remains intact.

Referring to FIG. 10, and with continued reference to FIG. 9, the operating mode transition process 1000 initializes or otherwise begins in response to detecting or otherwise identifying a desire to exit a particular operating mode. For example, the operating mode transition process 1000 may be initiated in response to a user manipulating the user interface 540, 608 to indicate a desire to exit one operating mode and enter another operating mode. In other embodiments, the operating mode transition process 1000 may be initiated in response to a particular operating mode automatically determining it should be exited and providing a corresponding indication to the supervisory module 910. For example, a maximum time limit may be imposed for one or more of the control modules 902, 904, 906, 908, with the respective control module 902, 904, 906, 908 implementing a timer and automatically notifying the supervisory control module 910 when the maximum time limit has been reached. Alternatively, the supervisory control module 910 may implement the appropriate timers and identify when the maximum time limit for a particular operating mode has been reached. Additionally, in some embodiments, one or more of the control modules 902, 904, 906, 908 may be configured to continually monitor or analyze its performance and detect or otherwise identify that its operating mode should be terminated when its performance appears to be unreliable. For example, the closed-loop control module 902 may automatically identify that the closed-loop operating mode should exit when one or more of the closed-loop control parameters appears to be invalid or unreliable, when measurement values from the sensing arrangement 504 appear to be invalid or unreliable, or the like.

In response to detecting or otherwise identifying a desire to exit a particular operating mode, the operating mode transition process 1000 receives or otherwise obtains operational information pertaining to the operating mode being exited along with clinical information pertaining to the physiological condition of the user (tasks 1002, 1004). In this regard, the supervisory module 910 obtains operational information from the control module 902, 904, 906, 908 associated with the operating mode currently being implemented. The operational information includes timer values (e.g., a delivery suspend time, a refractory period time, and the like), delivery status (e.g., whether or not delivery has been suspended), alert or event information (e.g., hypoglycemic events or alerts, hyperglycemic events or alerts, and the like), the reason the operating mode is terminating (e.g., manually-initiated, timeout, invalid control parameters and/or invalid measurement values, an anomalous condition, or the like), and other information characterizing the current instance of the operating mode. In exemplary embodiments, the supervisory module 910 obtains clinical information for the user, such as, for example, recent sensor glucose measurement values, predicted glucose measurement values, blood glucose reference measurement values, sensor calibration data, other historical data, and the like, from memory 606.

Using the operational information and the clinical information, the mode transition process 1000 identifies or otherwise determines the available operating modes for the transition destination (task 1006). In this regard, the supervisory module 910 utilizes the clinical information in conjunction with the operational information to identify which other operating modes are viable destinations for the transition while excluding any operating modes that are likely to violate one or more applicable constraints or otherwise are not likely to be viable. In this manner, the mode transition process 1000 increases the likelihood that the destination operating mode will not result in violations of applicable delivery control rules, constraints, limits, or the like. The mode transition process 1000 also reduces the likelihood that the destination operating mode will generate alerts that could degrade the user experience, and reduces the likelihood that the destination operating mode will automatically terminate or exit after being activated.

For example, in one or more embodiments, a maximum suspension time limit may be imposed on the infusion device 502 across all operating modes, with the supervisory module 910 excluding operating modes that would likely result in the minimum suspension time being violated based on the current suspend duration for the initial operating mode and the current or predicted glucose values for the user. For example, if transitioning from a closed-loop operating mode that has been suspending delivery for a period of time, and the user's predicted glucose value indicates the PLGM operating mode will likely suspend delivery for an additional amount of time such that the sum of the current suspend duration for the closed-loop operating mode and the expected suspend duration for the PLGM operating mode exceeds the maximum suspension time, the supervisory module 910 may exclude the PLGM operating mode from consideration as a possible destination operating mode.

As another example, a maximum insulin delivery limit over a particular timeframe (e.g., the preceding 24 hours) may be imposed, with the supervisory module 910 excluding operating modes that would likely result in the maximum insulin delivery limit being delivered based on the amount of insulin delivered for the initial operating mode and the current or predicted glucose values for the user. For example, if the difference between current and/or predicted glucose values for the user and the target glucose value for the closed-loop operating mode indicates that the closed-loop operating mode is likely to result in an amount of fluid delivery that would cause a maximum insulin delivery limit to be violated, the supervisory module 910 may exclude the closed-loop operating mode from consideration as a possible destination operating mode. In lieu of the closed-loop operating mode, in some embodiments, if the mode transition process 1000 is initiated in response to the maximum insulin delivery limit being reached during implementation of a current operating mode, a safe basal delivery mode (or hybrid closed-loop delivery mode) may be identified as a possible destination operating mode. The safe basal delivery mode may be realized as a hybrid closed-loop operating mode that configured to maintain a delivery rate that does not violate either the maximum insulin delivery limit or a minimum insulin delivery limit independent of the current or predicted measurements of the user's glucose. In this regard, the safe basal delivery mode may impose a maximum delivery rate that is less than or equal to the maximum insulin delivery limit divided by its applicable timeframe and impose a minimum delivery rate that is greater than the minimum insulin delivery limit divided by its applicable timeframe. Thus, the delivery commands generated in the safe basal delivery mode based on the difference between the current sensor glucose measurement value and the target glucose measurement value are bounded such that they will not violate applicable delivery limits.

Similarly, the supervisory module 910 may exclude operating modes that would likely result in the minimum insulin delivery limit being violated based on the amount of insulin delivered for the initial operating mode and the current or predicted glucose values for the user. For example, if the difference between current and/or predicted glucose values for the user and the target glucose value indicates the closed-loop operating mode is unlikely to deliver fluid for an amount of time that would cause the minimum insulin delivery limit to be violated, the supervisory module 910 may exclude the closed-loop operating mode from consideration as a possible destination operating mode. In some embodiments, if the mode transition process 1000 is initiated in response to the minimum insulin delivery limit being reached during implementation of a current operating mode, a safe basal delivery mode may be identified as a possible destination operating mode in lieu of the closed-loop operating mode.

As another example, the supervisory module 910 may exclude operating modes that utilize sensor glucose measurement values based on sensor health information. In this regard, recent sensor glucose measurement values or historical calibration information for the sensing arrangement 504 indicating that the sensing arrangement 504 may not be viable for the particular operating mode. In this regard, if the previous sensor glucose measurement values or historical calibration information indicates the sensing arrangement 504 is unhealthy or may require recalibration or replacement, the supervisory module 910 prevents entry of operating modes that would otherwise be relying potentially unreliable sensor measurement values. For example, the supervisory module 910 may exclude the closed-loop operating mode from consideration as a possible destination operating mode if a difference between the current sensor glucose measurement value and a predicted glucose value is greater than a threshold value, a calibration factor for the sensing arrangement 504 has expired, communications with the sensing arrangement 504 have been interrupted, a difference between the current calibration factor and the preceding calibration factor is greater than a threshold amount (e.g., a difference of more than 35%), or a difference between reference blood glucose measurement value and the corresponding sensor measurement value used for the current calibration factor is greater than a threshold amount (e.g., the sensor measurement value is more than 35% greater than or less than the reference blood glucose measurement value). In other embodiments, an operating mode that utilizes sensor glucose measurement values may be excluded when a duration of time that has elapsed since the most recent calibration exceeds a threshold value.

In one exemplary embodiment, a desired maximum number of alerts over a particular timeframe (e.g., the preceding 24 hours) could be designated by the user, with the supervisory module 910 excluding operating modes that would likely result in that maximum number of alerts being exceeded. For example, the operational information obtained by the supervisory module 910 may include a current number of user notifications or alerts that have been generated by the current operating mode (e.g., by the respective control module 902, 904, 906, 908 implementing a corresponding counter). The supervisory module 910 may determine an expected number of user notifications or alerts to be generated by a particular operating mode based on the current and/or predicted glucose values for the user, and exclude that operating mode from the set of possible destination operating modes when the sum of the expected number of alerts and the current number of alerts exceeds the maximum number chosen by the user.

In one or more embodiments, the supervisory module 910 excludes operating modes based on the status of user notifications previously generated by the infusion device 502. For example, if a user notification has been generated that indicates the user should recalibrate or replace the sensing arrangement 504, and the user has not responded to the user notification by recalibrating or replacing the sensing arrangement 504 within a threshold amount of time (e.g., 90 minutes), the supervisory module 910 may exclude the closed-loop operating mode or other operating modes that rely on the sensing arrangement 504 from consideration as possible destination modes until the user responds to the notification.

Additionally, in one or more embodiments, the supervisory module 910 performs one or more diagnostic checks for the potential destination operating modes to verify or otherwise confirm the potential destination operating modes will be viable, in a similar manner as described above in the context of FIG. 8 (e.g., tasks 810, 812, 814). In this regard, if the operational information and/or the clinical information indicates that an operating mode is unlikely to be viable for the entirety of its expected or foreseeable duration, the supervisory module 910 may exclude that operating mode from consideration. For example, the supervisory module 910 may verify or otherwise determine that the control parameters of the closed-loop operating mode can be calculated and will be valid for the expected duration before including the closed-loop operating mode in the group of potential destination operating modes. In this regard, if transitioning to the closed-loop operating mode may require affirmative user action (e.g., the user manipulating the blood glucose meter 530 to obtain one or more blood glucose measurement values), the supervisory module 910 may exclude the closed-loop operating mode from the potential destination operating modes. In some embodiments, the supervisory module 910 may also generate or otherwise provide one or more user notifications of recommended remedial actions to improve the future viability of an excluded operating mode in a similar manner as described above (e.g., task 816).

Still referring to FIG. 10, after identifying the available operating modes for a potential transition destination, the mode transition process 1000 continues by identifying or otherwise selecting a destination operating mode from among the group of available operating modes (task 1008). In exemplary embodiments, the supervisory module 910 automatically selects the available operating mode to that is most preferable or most highly ranked based on device settings or user preferences maintained in memory 606. In this regard, the user may manipulate a user interface 540, 608 to establish a hierarchical ordering of the operating modes in the user's order of preference, with the hierarchical information being stored in the memory 606 along with other user preferences. For example, the user may identify the closed-loop operating mode as the most preferred operating mode, followed by the PLGM operating mode as the next most preferred operating mode, the LGS operating mode as the next most preferred operating mode, and the open-loop operating mode as the least preferred operating mode. In other embodiments, default settings for the infusion device 102, 200, 502 may specify a default hierarchical order of operating modes. It should be appreciated, however, that the subject matter described herein is not limited to any particular type of selection criteria used to identify the most preferable operating mode from among the available operating modes.

After selecting the destination operating mode, the mode transition process 1000 continues by identifying or otherwise determining the types or subset of operational information pertaining to the current operating mode to be provided to the destination operating mode and providing that identified operational information to the destination operating mode (tasks 1010, 1012). In this regard, the supervisory module 910 passes at least a portion of the operational information obtained from the current operating mode control module 902, 904, 906, 908 to the destination module 902, 904, 906, 908 such that the implementation of the destination operating mode does not violate any delivery rules, constraints, limits, or the like. For example, the supervisory module 910 may obtain the current refractory period timer value, the current suspend duration timer value, or the like, from the control module 902, 904, 906, 908 corresponding to the current operating mode and provide those values to the control module 902, 904, 906, 908 corresponding to the destination operating mode to ensure that the destination operating mode does not violate a minimum refractory time period between suspending delivery, a maximum suspend duration, a minimum suspend duration, or the like. Additionally, the supervisory module 910 may provide the exit reason for the current operating mode, the current delivery status, information about alerts or events that occurred during the current operating mode, active insulin estimates, sensor health status and/or calibration information, and/or other historical delivery information to the destination operating mode control module 902, 904, 906, 908. The destination operating mode generates dosage commands in accordance with the operational information received from the preceding operating mode to provide a relatively seamless transition among operating modes.

Referring again to FIG. 10, the mode transition process 1000 continues by providing, to the infusion device motor control module, the dosage (or delivery) commands generated by the destination operating mode in accordance with the provided operational information (task 1014). In this regard, the supervisory module 910 signals, commands or otherwise operates the command multiplexer 920 to output dosage commands generated by the destination operating mode control module 902, 904, 906, 908 and cease outputting dosage commands from the previously-active operating mode. For example, to transition from the closed-loop operating mode to the PLGM operating mode, the supervisory module 910 signals, commands or otherwise operates the command multiplexer 920 to output dosage commands generated by the PLGM control module 904 instead of the closed-loop control module 902. Additionally, in some embodiments, the supervisory module 910 may assert or otherwise provide interrupt signals that indicate, to the respective control modules 902, 904, 906, 908, whether or not the respective control module 902, 904, 906, 908 should generate dosage commands. For example, the supervisory module 910 may deactivate the closed-loop control module 902 (e.g., by providing a logical high interrupt signal to the closed-loop control module 902) and activate the PLGM control module 904 (e.g., by providing a logical low interrupt signal to the PLGM control module 904) while maintaining the other control modules 906, 908 deactivated.

Referring to FIG. 9, in accordance with one embodiment, when transitioning from the closed-loop operating mode to the PLGM operating mode, the supervisory module 910 obtains information identifying the exit reason (e.g., manual or auto), the amount of time delivery has been suspended in the preceding sixty minutes, and the current value of the closed-loop refractory timer from the closed-loop control module 902. In some embodiments, the supervisory module 910 calculates the refractory time based on the amount of continuous delivery commands that precede the transition. The supervisory module 910 provides the obtained values and information to the PLGM control module 904, and thereafter, the PLGM control module 904 generates dosage commands in accordance with the operational information from the closed-loop control module 902.

For example, the PLGM control module 904 may set its refractory timer to the value of the closed-loop refractory timer and maintain delivery until the total refractory time exceeds the minimum refractory time period before suspending delivery. Thus, even if the user's predicted glucose level is below the predictive suspend threshold, the PLGM control module 904 may continue providing dosage commands that result in a basal rate of infusion until the value of the PLGM refractory timer is greater than or equal to the minimum refractory time period. In some embodiments, the PLGM control module 904 may utilize the exit reason to determine whether to continue providing dosage commands until the value of the PLGM refractory timer is greater than or equal to the minimum refractory time period. For example, if the exit reason is manual (e.g., the user manually transitioned the infusion device 502 to the PLGM mode), the PLGM control module 904 may provide dosage commands until the minimum refractory time period is observed, however, if the exit reason is automatic, the PLGM control module 904 may suspend dosage commands before the minimum refractory time period is observed and reset the PLGM refractory timer as appropriate.

In some embodiments, the sensor health status and/or calibration information, estimated active insulin information, and/or other operational information from the closed-loop operating mode may be utilized in conjunction with the exit reason when determining whether to observe the minimum refractory time period in the PLGM operating mode. For example, the PLGM control module 904 may allow dosage commands to be suspended only if the sensing arrangement 504 was calibrated less than a threshold amount of time before the transition (e.g., within the last hour) and the estimated active insulin is greater than a safe threshold value, which may be manually set by a user or a default value maintained by the infusion device 502. Thus, the minimum refractory time period may still be observed for an automatic transition if the sensing arrangement 504 was not calibrated recently or the estimated active insulin is too low. Conversely, the PLGM control module 904 may automatically suspend delivery when the refractory time from the closed-loop control module 902 is less than the minimum refractory time period in response to determining the active insulin estimate from the closed-loop control module 902 is greater than the threshold value.

Similarly, if delivery is currently being suspended, the PLGM control module 904 may set its delivery suspend timer to the value of the closed-loop suspend timer (e.g., the amount of time delivery has been suspended in the preceding sixty minutes). Thus, even if the user's predicted glucose level is below the predictive suspend threshold, the PLGM control module 904 may begin providing dosage commands once the value of the PLGM delivery suspend timer is greater than the maximum suspension time period. Additionally, in some embodiments, the exit reason may be utilized by the PLGM control module 904 to determine whether to suspend delivery or resume delivery, either independently or in conjunction with the sensor health status and/or calibration information, estimated active insulin information, and/or other operational information, in a similar manner as described above. For example, if the sensing arrangement 504 was calibrated less than a threshold amount of time before the transition (e.g., within the last hour) and the estimated active insulin is less than a threshold value, the PLGM control module 904 may resume providing dosage commands even though the maximum suspension time period may not have been met.

When transitioning from the closed-loop operating mode to the LGS operating mode, the supervisory module 910 obtains information identifying the exit reason (e.g., manual or auto), the amount of time delivery has been suspended in the preceding sixty minutes, and the current value of the closed-loop refractory timer from the closed-loop control module 902 and provides the obtained values and information to the LGS control module 906 for generating dosage commands in accordance therewith, in a similar manner as described above for transitions to the PLGM operating mode.

In another example embodiment, when transitioning from the closed-loop operating mode to the open-loop operating mode, the supervisory module 910 may only provide the refractory timer values from the closed-loop control module 902 to the open-loop control module 908. In such an embodiment, the open-loop control module 908 provides dosage commands that result in an open-loop basal rate of infusion while dynamically updating the refractory timer value for a subsequent transition to another operating mode. In this regard, the refractory timer value is updated so that if the infusion device 502 subsequently transitions from the open-loop operating mode to another operating mode where delivery could be suspended, the minimum refractory period is still observed by the control module 902, 904, 906 associated with that subsequent operating mode before delivery is suspended. In other embodiments, in lieu of providing the refractory time information to the open-loop control module 908, the supervisory module 910 may independently manage and dynamically update the refractory time information, and subsequently provide the refractory time information to another destination control module 902, 904, 906 when transitioning from the open-loop operating mode. Similarly, in some embodiments, the supervisory module 910 may provide suspension information to the open-loop control module 908 (e.g., the amount of time delivery was suspended over a preceding time interval) for dynamically updating the suspension time information to ensure any maximum suspension limits are still observed by a control module 902, 904, 906 associated with that subsequent operating mode. Alternatively, the supervisory module 910 may also independently manage and dynamically update the refractory time information, and subsequently provide the refractory time information to a destination control module 902, 904, 906 when transitioning from the open-loop operating mode.

In other exemplary embodiments, when transitioning from the PLGM operating mode or the LGS operating mode to the closed-loop operating mode, the supervisory module 910 obtains information identifying the exit reason (e.g., manual or auto) and the current value of the respective refractory timer from the respective control module 904, 906 and provides the obtained values and information to the closed-loop control module 902. In this regard, the closed-loop control module 902 sets its refractory timer to the value of the refractory timer of the respective control module 904, 906 and may maintain delivery until the total refractory time exceeds the minimum refractory time period before suspending delivery. In other embodiments, the closed-loop control module 902 may suspend delivery even though the total refractory time is less than the minimum refractory time period. For example, the closed-loop control module 902 may obtain sensor calibration information from the preceding operating mode and determine whether a duration of time that has elapsed since the most recent calibration exceeds a threshold value corresponding to the reliable lifetime of a calibration factor for purposes of the closed-loop mode. When the duration of time that has elapsed since the most recent calibration exceeds the threshold value, the closed-loop control module 902 may generate a notification via the user interface 540 that prompts the user to obtain a new blood glucose reference measurement value for recalibrating the sensing arrangement 504 upon transitioning to the closed-loop mode. In response to the user manipulating the blood glucose meter 530 to obtain a new blood glucose reference measurement value, and the new blood glucose reference measurement value indicates delivery should be suspended, the closed-loop control module 902 may suspend delivery even though the total refractory time does not exceed the minimum refractory time period. Alternatively, in the absence of a new blood glucose reference measurement value that indicates delivery should be suspended, the closed-loop control module 902 may generate dosage commands to provide a minimum basal rate of infusion while the closed-loop refractory timer value is less than the minimum refractory time period even though the user's current glucoses measurement value may be less than the target glucose value for the closed-loop control system.

In yet other exemplary embodiments, when transitioning from the open-loop operating mode to another operating mode, the supervisory module 910 obtains information identifying the exit reason (e.g., manual or auto) and the current value of the refractory timer from the open-loop module 908 and provides the obtained value to the particular destination operating mode control module 902, 904, 906. In this regard, when transitioning from the open-loop operating mode, the destination operating mode control module 902, 904, 906 sets its refractory timer to the value provided by the supervisory module 910 to maintain delivery until the total refractory time exceeds the minimum refractory time period before allowing delivery to be suspended.

It will be appreciated that in practice there are numerous different types of information that may be exchanged among control modules 902, 904, 906, 908 to achieve a desired manner of transitioning and comply with the particular constraints, rules, and/or limits for a particular application. Accordingly, the above examples are provided merely to aid in understanding of the subject matter and are not intended to be limiting.

It should also be noted that in practice, the diagnosis process 800 of FIG. 8 and the mode transition process 1000 of FIG. 10 may be implemented independently, or alternatively, in conjunction with one another. In this regard, the diagnosis process 800 may be performed to increase the likelihood of availability of the various operating modes when the mode transition process 1000 is performed at the expected start time, thereby increasing the likelihood of the supervisory module 910 identifying more than one potential destination operating mode (e.g., task 1006) when the mode transition process 1000 is performed. By increasing the availability of the various operating modes, a desired level of control of the user's physiological condition can be more readily achieved in a manner that minimizes undesirable disruptions during implementation of the desired operating mode, thereby improving the user experience.

To briefly summarize, the subject matter described herein facilitates transitioning between operating modes in a manner that enhances the user experience (e.g., by enabling the user to proactively increase viability of a desired operating mode and/or excluding operating modes that are likely to generate alerts from possible destinations for automatic transitions) and ensures compliance with applicable delivery control rules and other constraints (e.g., by excluding operating modes that are otherwise likely to result in a violation and transferring timer and/or counter values across operating modes).

For the sake of brevity, conventional techniques related to glucose sensing and/or monitoring, closed-loop glucose control, predictive glucose management, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating an infusion device operable to deliver fluid to a user, the method comprising:
   operating the infusion device to deliver the fluid in an automated manner in accordance with a first operating mode of a plurality of different operating modes, each operating mode of the plurality of different operating modes generating commands for delivering the fluid to the user in an automated manner in accordance with a different delivery control scheme associated therewith;
   obtaining operational information pertaining to the operating of the infusion device in accordance with the first operating mode, wherein the operational information includes a current value for a suspension timer of the first operating mode;

obtaining clinical information pertaining to the user;
automatically selecting a destination operating mode different than the first operating mode from among remaining operating modes of the plurality of different operating modes based at least in part on the operational information and the clinical information;
transitioning operation of the infusion device from the first operating mode to the destination operating mode, wherein the destination operating mode is initialized using at least a portion of the operational information by setting a second suspension timer, different than the first suspension timer, of the destination operating mode to the current value for the suspension timer of the first operating mode; and
operating the infusion device to deliver the fluid in accordance with the destination operating mode in a manner that is influenced by the current value for the second suspension timer.

2. The method of claim 1, wherein:
the first operating mode comprises one of a closed-loop operating mode, a predictive low glucose management operating mode, and a low glucose suspend operating mode; and
the destination operating mode comprises a different one of the closed-loop operating mode, the predictive low glucose management operating mode, and the low glucose suspend operating mode.

3. The method of claim 1, wherein:
the first operating mode comprises an overnight closed-loop operating mode; and
the destination operating mode comprises one of a predictive low glucose management operating mode, a low glucose suspend operating mode, a safe basal delivery mode, and an open-loop operating mode.

4. The method of claim 1, the first operating mode having a first control module associated therewith and the destination operating mode having a second control module associated therewith, wherein transitioning operation of the infusion device from the first operating mode to the destination operating mode comprises a supervisory control module operating a command multiplexer to output second dosage commands generated by the second control module and cease outputting first dosage commands generated by the first control module.

5. The method of claim 1, the first operating mode having a first control module associated therewith and the destination operating mode having a second control module associated therewith, wherein transitioning operation of the infusion device from the first operating mode to the destination operating mode comprises a supervisory control module providing the portion of the operational information from the first control module to the second control module.

6. The method of claim 1, the portion of the operational information comprising an exit reason for the first operating mode, wherein operating the infusion device to deliver the fluid in accordance with the destination operating mode in a manner that is influenced by the portion of the operational information pertaining to the first operating mode comprises the destination operating mode determining whether to suspend or resume delivery of the fluid based at least in part on the exit reason.

7. The method of claim 1, wherein:
the remaining operating modes comprise a set of one or more possible operating modes of the plurality of different operating modes; and
automatically selecting the destination operating mode comprises:
identifying the set of one or more possible operating modes of the plurality of different operating modes by excluding, from the set, an operating mode of the plurality of different operating modes when the clinical information indicates the operating mode will violate a delivery control rule based on the operational information; and
selecting the destination operating mode from the set.

8. The method of claim 7, the clinical information including a current glucose measurement value and the current value for the suspension timer comprises a suspended delivery time for the first operating mode, wherein excluding the operating mode comprises excluding the operating mode when the current glucose measurement value indicates the operating mode will violate a suspension time limit based on the suspended delivery time.

9. The method of claim 7, the clinical information including a current glucose measurement value and an insulin delivered, wherein excluding the operating mode comprises excluding the operating mode when the current glucose measurement value indicates the operating mode will violate an insulin delivery limit.

10. The method of claim 1, wherein:
the remaining operating modes comprise a set of one or more possible operating modes of the plurality of different operating modes; and
automatically selecting the destination operating mode comprises:
identifying the set of one or more possible operating modes of the plurality of different operating modes by excluding, from the set, an operating mode of the plurality of different operating modes when the clinical information indicates the operating mode will generate a user notification; and
selecting the destination operating mode from the set.

11. The method of claim 1, wherein:
the operational information includes a first number of user notifications generated by the first operating mode;
the remaining operating modes comprise a set of one or more possible operating modes of the plurality of different operating modes; and
automatically selecting the destination operating mode comprises:
determining an operating mode of the plurality of different operating modes is likely to generate a second number of user notifications based on the clinical information;
identifying the set of one or more possible operating modes of the plurality of different operating modes by excluding, from the set, the operating mode of the plurality of different operating modes when a sum of the first number and the second number is greater than a threshold number of user notifications; and
selecting the destination operating mode from the set.

12. The method of claim 1, wherein:
the remaining operating modes comprise a set of one or more possible operating modes of the plurality of different operating modes; and
automatically selecting the destination operating mode comprises:
identifying the set of one or more possible operating modes of the plurality of different operating modes by excluding, from the set, an operating mode of the plurality of different operating modes when the clinical information indicates the operating mode will automatically terminate; and
selecting the destination operating mode from the set.

13. The method of claim 1, wherein:
the remaining operating modes comprise a set of one or more possible operating modes of the plurality of different operating modes; and
automatically selecting the destination operating mode comprises:
identifying the set of one or more possible operating modes of the plurality of different operating modes by excluding, from the set, an operating mode of the plurality of different operating modes in response to determining the operating mode is not viable for an expected duration based at least in part on the clinical information; and
selecting the destination operating mode from the set.

14. The method of claim 1, wherein:
the portion of the operational information includes sensor health information;
the remaining operating modes comprise a set of one or more possible operating modes of the plurality of different operating modes; and
automatically selecting the destination operating mode comprises:
identifying the set of one or more possible operating modes of the plurality of different operating modes by excluding, from the set, an operating mode of the plurality of different operating modes based on the sensor health information; and
selecting the destination operating mode from the set.

15. The method of claim 14, wherein excluding the operating mode comprises excluding the operating mode that utilizes sensor glucose measurement values when at least one of:
a first difference between a current sensor glucose measurement value and a predicted glucose value is greater than a first threshold;
a calibration factor for a sensing arrangement has expired;
communications with the sensing arrangement have been interrupted;
a second difference between a current calibration factor and a preceding calibration factor is greater than a second threshold;
a third difference between a reference blood glucose measurement value and a corresponding sensor measurement value used for the current calibration factor is greater than a third threshold; or
a duration of time that has elapsed since a most recent calibration exceeds a fourth threshold.

16. The method of claim 1, wherein operating the infusion device to deliver the fluid in accordance with the destination operating mode comprises the destination operating mode generating dosage commands in an automated manner once a value of the second suspension timer is greater than a maximum suspension time period.

17. An infusion device comprising:
a data storage element to maintain operational information characterizing a current instance of a first operating mode of a plurality of different operating modes and clinical information pertaining to a user, wherein the operational information includes a current value for a suspension timer of the first operating mode;
a motor operable to deliver fluid to a body of the user, the fluid influencing a physiological condition of the user; and
a control system coupled to the motor and the data storage element to:
operate the motor to deliver the fluid in an automated manner in accordance with the first operating mode;
automatically select a destination operating mode different than the first operating mode from among remaining operating modes of the plurality of different operating modes based at least in part on the operational information characterizing the current instance of the first operating mode and the clinical information; and
transition from the first operating mode to the destination operating mode to operate the motor to deliver the fluid in an automated manner in accordance with the destination operating mode, wherein:
the destination operating mode is initialized using at least a portion of the operational information characterizing the current instance of the first operating mode by setting a second suspension timer, different than the first suspension timer, of the destination operating mode to the current value for the suspension timer of the first operating mode; and
each different operating mode of the plurality of different operating modes generates commands for delivering the fluid to the user in an automated manner in accordance with a different delivery control scheme.

18. The infusion device of claim 17, further comprising:
a first control module associated with the first operating mode; and
a second control module associated with the destination operating mode, wherein the control system transitions from the first operating mode to the destination operating mode by providing the portion of the operational information pertaining to the first operating mode to the second control module.

19. The infusion device of claim 17, further comprising:
a first control module associated with the first operating mode;
a second control module associated with the destination operating mode; and
a command multiplexer coupled to the first control module and the second control module, wherein the control system is coupled to the command multiplexer and transitions from the first operating mode to the destination operating mode by operating the command multiplexer to output second dosage commands generated by the second control module and cease outputting first dosage commands generated by the first control module.

20. A computer-readable medium having instructions stored thereon that are executable by a processor to:
operate an infusion device to deliver a fluid in an automated manner in accordance with a first operating mode of a plurality of different operating modes, each operating mode of the plurality of different operating modes generating commands for delivering the fluid to a user in an automated manner in accordance with a different delivery control scheme associated therewith;
obtain operational information pertaining to the operating of the infusion device in accordance with the first operating mode, wherein the operational information includes a current value for a suspension timer of the first operating mode;
obtain clinical information pertaining to the user;
automatically select a destination operating mode different than the first operating mode from among remaining operating modes of the plurality of different operating modes based at least in part on the operational information and the clinical information;

transition operation of the infusion device from the first operating mode to the destination operating mode, wherein the destination operating mode is initialized using at least a portion of the operational information by setting a second suspension timer, different than the first suspension timer, of the destination operating mode to the current value for the suspension timer of the first operating mode; and operate the infusion device to deliver the fluid in accordance with the destination operating mode in a manner that is influenced by the current value for the second suspension timer.

\* \* \* \* \*